(12) United States Patent
Farrington et al.

(10) Patent No.: US 10,531,657 B2
(45) Date of Patent: Jan. 14, 2020

(54) LOW TEMPERATURE SPECIMEN CARRIERS AND RELATED METHODS

(71) Applicant: CooperSurgical, Inc., Trumbull, CT (US)

(72) Inventors: Richard I. Farrington, Seymour, CT (US); Patrick N. Gutelius, Monroe, CT (US); James R. Parys, Wallingford, CT (US)

(73) Assignee: CooperSurgical, Inc., Trumbull, CT (US)

( * ) Notice: Subject to any disclaimer, the term of this patent is extended or adjusted under 35 U.S.C. 154(b) by 463 days.

(21) Appl. No.: 15/275,706

(22) Filed: Sep. 26, 2016

(65) Prior Publication Data
US 2017/0156312 A1    Jun. 8, 2017

Related U.S. Application Data

(60) Provisional application No. 62/263,894, filed on Dec. 7, 2015, provisional application No. 62/292,620, filed on Feb. 8, 2016.

(51) Int. Cl.
*A01N 1/02* (2006.01)
*B01L 3/00* (2006.01)
*B01L 7/00* (2006.01)

(52) U.S. Cl.
CPC ........... *A01N 1/0268* (2013.01); *A01N 1/021* (2013.01); *A01N 1/0284* (2013.01);
(Continued)

(58) Field of Classification Search
CPC .............................. A01N 1/0268; A01N 1/021
See application file for complete search history.

(56) References Cited

U.S. PATENT DOCUMENTS

| 2,994,349 A | 8/1961 | Demos |
| 3,212,207 A | 10/1965 | Searing |

(Continued)

FOREIGN PATENT DOCUMENTS

| DE | 3802087 | 7/1989 | ............... G01N 1/00 |
| DE | 101 54 431 | 5/2003 | ............... G01N 9/12 |

(Continued)

OTHER PUBLICATIONS

Cryolock—Home Page; http://cryolock.info/cryolock/index.php; downloaded on Dec. 7, 2015.

(Continued)

*Primary Examiner* — Brian M King
(74) *Attorney, Agent, or Firm* — Fish & Richardson P.C.

(57) ABSTRACT

A specimen carrier includes an elongate member defining an external sealing surface and a support surface upon which a specimen can be carried, the elongate member including a first material having a first coefficient of thermal expansion. The specimen carrier further includes a cap configured to be passed over a portion of the elongate member to close a region of the cap that surrounds the specimen when the cap is passed over the portion of the elongate member, the cap defining an internal sealing surface formed complementary to the external sealing surface, and the cap including a second material having a second coefficient of thermal expansion that is greater than the first coefficient of thermal expansion. When the elongate member and cap are together placed in a cooling substance, the internal sealing surface of the cap compresses the external sealing surface of the elongate member to form a hermetic seal.

21 Claims, 9 Drawing Sheets

(52) U.S. Cl.
CPC ............ *B01L 3/50825* (2013.01); *B01L 7/50* (2013.01); *B01L 2200/0689* (2013.01); *B01L 2300/0832* (2013.01); *B01L 2300/1894* (2013.01)

(56) References Cited

U.S. PATENT DOCUMENTS

| | | |
|---|---|---|
| 3,233,785 A | 2/1966 | Burke |
| 4,134,359 A | 1/1979 | Redpath |
| 4,184,483 A | 1/1980 | Greenspan |
| 4,515,697 A | 5/1985 | Elmaleh et al. |
| 4,559,298 A | 12/1985 | Fahy |
| 4,567,847 A | 2/1986 | Linner |
| 4,688,387 A | 8/1987 | Conaway |
| 4,707,998 A | 11/1987 | Linner et al. |
| 4,712,607 A | 12/1987 | Lindemans et al. |
| 4,779,768 A | 10/1988 | St. Amand |
| 4,799,358 A | 1/1989 | Knopf et al. |
| 4,817,397 A | 4/1989 | Grischenko et al. |
| 4,877,037 A | 10/1989 | Ko et al. |
| 4,939,884 A | 7/1990 | Peters |
| 4,978,504 A | 12/1990 | Nason |
| 5,026,342 A | 6/1991 | Hammerstedt et al. |
| 5,036,904 A | 8/1991 | Kanda et al. |
| 5,067,532 A | 11/1991 | Lang et al. |
| 5,078,968 A | 1/1992 | Nason |
| 5,160,312 A | 11/1992 | Voelkel |
| 5,163,441 A | 11/1992 | Monthony et al. |
| 5,190,880 A | 3/1993 | Cassou et al. |
| 5,217,693 A | 6/1993 | Anderson et al. |
| 5,256,537 A | 10/1993 | Phillips et al. |
| 5,261,870 A | 11/1993 | Hammerstedt et al. |
| 5,283,170 A | 2/1994 | Cassou et al. |
| 5,334,348 A | 8/1994 | Saito et al. |
| 5,357,762 A | 10/1994 | Charton |
| 5,358,931 A | 10/1994 | Rubinsky et al. |
| 5,392,943 A | 2/1995 | Delatte et al. |
| 5,402,915 A | 4/1995 | Hogan |
| 5,493,865 A | 2/1996 | Wohlwend |
| 5,545,562 A | 8/1996 | Cassou et al. |
| 5,665,308 A | 9/1997 | Watanabe |
| 5,681,740 A | 10/1997 | Messier et al. |
| 5,894,733 A | 4/1999 | Brodner |
| 5,952,168 A | 9/1999 | Wowk et al. |
| 5,965,438 A | 10/1999 | Kadkade et al. |
| 6,057,151 A | 5/2000 | Greenwood et al. |
| 6,176,089 B1 | 1/2001 | Bouche |
| 6,194,137 B1 | 2/2001 | Khirabadi et al. |
| 6,242,248 B1 | 6/2001 | Rozga et al. |
| 6,274,303 B1 | 8/2001 | Wowk et al. |
| 6,303,285 B1 | 10/2001 | Woelders |
| 6,337,205 B1 | 1/2002 | Wisniewski |
| 6,500,608 B2 | 12/2002 | Forest et al. |
| 6,514,216 B2 | 2/2003 | Inoue et al. |
| 6,519,954 B1 | 2/2003 | Prien et al. |
| 6,533,933 B1 | 3/2003 | Stankowski et al. |
| 6,615,592 B2 | 9/2003 | Prien et al. |
| 6,716,182 B2 | 4/2004 | Inoue |
| 6,740,484 B1 | 5/2004 | Khirabadi et al. |
| 6,858,424 B2 | 2/2005 | Wisniewski |
| 6,982,172 B2 | 1/2006 | Yang et al. |
| 7,087,370 B2 | 8/2006 | Forest et al. |
| 7,108,909 B1 | 9/2006 | Perlman et al. |
| 7,157,222 B2 | 1/2007 | Khirabadi et al. |
| 7,270,946 B2 | 9/2007 | Brockbank et al. |
| 7,278,278 B2 | 10/2007 | Wowk et al. |
| 7,281,550 B2 | 10/2007 | Ziegler |
| 7,310,954 B2 | 12/2007 | Miki |
| 7,316,896 B2 | 1/2008 | Kuwayama et al. |
| 7,748,165 B2 | 7/2010 | Harvey et al. |
| 7,845,245 B2 | 12/2010 | Hayles et al. |
| 7,943,293 B2 | 5/2011 | Cecchi |
| 7,947,497 B2 | 5/2011 | Yoon et al. |
| 8,017,311 B2 | 9/2011 | Brockbank et al. |
| 8,030,063 B2 | 10/2011 | Kader et al. |
| 8,256,232 B2 | 9/2012 | Burg |
| 8,266,872 B2 | 9/2012 | Ehrsam et al. |
| 8,293,462 B2 | 10/2012 | Eto et al. |
| 8,372,633 B2 | 2/2013 | Clairaz et al. |
| 8,513,622 B2 | 8/2013 | Hartfield |
| 8,633,023 B2 | 1/2014 | Du et al. |
| 8,852,078 B2 | 10/2014 | Prather et al. |
| 8,859,283 B2 | 10/2014 | Stojanov |
| 8,956,855 B2 | 2/2015 | Cognard et al. |
| 9,005,886 B2 | 4/2015 | Sanchez Gutierrez et al. |
| 9,142,384 B2 | 9/2015 | Schampers et al. |
| 9,211,171 B2 | 12/2015 | Ehrsam et al. |
| 9,297,499 B2 | 3/2016 | Jimenez-Rios et al. |
| 2002/0115054 A1 | 8/2002 | Forest et al. |
| 2006/0234204 A1 | 10/2006 | Forest et al. |
| 2008/0057040 A1 | 3/2008 | Crook et al. |
| 2008/0169037 A1 | 7/2008 | Ziegler |
| 2008/0202628 A1 | 8/2008 | Ehrsam et al. |
| 2008/0233633 A1 | 9/2008 | Clairaz et al. |
| 2009/0017440 A1 | 1/2009 | Pribenszky et al. |
| 2009/0123996 A1 | 5/2009 | Chin |
| 2009/0255938 A1* | 10/2009 | Fuja ................ A01N 1/0242 220/560.05 |
| 2010/0003662 A1 | 1/2010 | Kagawa et al. |
| 2010/0151570 A1* | 6/2010 | Kader ................ A01N 1/02 435/374 |
| 2010/0179377 A1 | 7/2010 | Hagby |
| 2011/0105359 A1* | 5/2011 | Czerwinski ........... A01N 1/02 506/10 |
| 2011/0129811 A1 | 6/2011 | Tao |
| 2013/0137080 A1 | 5/2013 | Henderson et al. |
| 2013/0165744 A1 | 6/2013 | Carson et al. |
| 2013/0344473 A1* | 12/2013 | Deutsch ............. B01L 3/5085 435/2 |
| 2014/0011182 A1 | 1/2014 | Van Sickle et al. |
| 2014/0158695 A1* | 6/2014 | Jimenez-Rios ...... A01N 1/0268 220/560.04 |
| 2014/0212962 A1 | 7/2014 | Inoue |
| 2014/0234956 A1 | 8/2014 | Inoue |

FOREIGN PATENT DOCUMENTS

| | | | |
|---|---|---|---|
| DE | 699 13 186 | 9/2004 | ............ A01N 1/02 |
| DE | 601 03 498 | 6/2005 | ............ A01N 1/02 |
| EP | 0 085 629 | 4/1988 | ............ B01D 21/00 |
| EP | 0 364 633 | 4/1990 | ............ G01N 1/28 |
| EP | 0 181 235 | 4/1991 | ............ A01N 1/02 |
| EP | 0 480 109 | 1/1995 | ............ A61D 19/02 |
| EP | 0 635 305 | 1/1995 | ............ B01L 3/14 |
| EP | 0 562 947 | 1/1997 | ............ G09F 3/02 |
| EP | 1 121 015 | 11/2003 | ............ A01N 1/02 |
| EP | 0 997 114 | 2/2004 | ............ A61D 19/00 |
| EP | 1 246 524 | 5/2004 | ............ A01N 1/02 |
| EP | 2 156 735 | 2/2010 | ............ A01N 1/02 |
| EP | 1 928 600 | 11/2010 | ............ B01L 3/00 |
| EP | 2 353 383 | 8/2011 | ............ A01N 1/02 |
| EP | 1 928 601 | 5/2012 | ............ B01L 3/00 |
| EP | 2 224 800 | 1/2013 | ............ A01N 1/02 |
| EP | 1 838 445 | 11/2013 | ............ G01L 1/42 |
| FR | 2 574 919 | 6/1986 | ............ F28D 7/10 |
| FR | 2 727 618 | 6/1996 | ............ A61B 17/36 |
| FR | 2 810 535 | 10/2002 | ............ A61D 19/02 |
| FR | 2 886 931 | 8/2007 | ............ B67D 5/00 |
| FR | 2 891 166 | 11/2007 | ............ B01L 3/00 |
| FR | 2 891 165 | 1/2008 | ............ B01L 3/00 |
| FR | 2 912 727 | 7/2013 | ............ B65D 1/02 |
| GB | 2 417 961 | 3/2008 | ............ A01N 1/02 |
| GB | 2 429 717 | 4/2009 | ............ C12N 5/08 |
| JP | 7-260777 | 10/1995 | ............ G01N 33/48 |
| JP | 7-260778 | 10/1995 | ............ G01N 33/48 |
| JP | 10-243951 | 9/1998 | ............ A61D 19/02 |
| JP | 2597948 | 5/1999 | ............ G01N 33/48 |
| JP | 2000-189155 | 7/2000 | ............ C12N 1/04 |
| JP | 2002-315573 | 10/2002 | ............ C12N 5/06 |
| JP | 2004-329202 | 11/2004 | ............ A01K 67/02 |
| JP | 2006-271395 | 10/2006 | ............ C12M 3/00 |
| WO | WO 83/02386 | 7/1983 | ............ A01N 1/02 |
| WO | WO 91/03935 | 4/1991 | ............ A01N 1/02 |

(56) References Cited

FOREIGN PATENT DOCUMENTS

| WO | WO 99/08513 | 2/1999 | ............... A01N 1/02 |
| WO | WO 99/11121 | 3/1999 | ............... A01N 1/02 |
| WO | WO 00/21365 | 4/2000 | ............... A01N 1/02 |
| WO | WO 2014/088859 | 6/2014 | ............... A01N 1/02 |

OTHER PUBLICATIONS

Final Search Report for Invalidity Search Surrounding IVF Transfer Instrument (Sep. 14, 2016) (3 pages).

Kasai, "Cryopreservation of Mammalian Embryos", *Molecular Biotechnology*, vol. 7, pp. 173-179 (1997).

Kitazato Dibimed, *Vitrification Cryotop*; "The Cryotop Method", http://www.kitazato-dibimed.com/ver/11/Vitrification-Cryotop.html; downloaded on Dec. 7, 2015.

Lane et al., "Vitrification of mouse and human blastocysts using a novel cryoloop container-less technique", *Fertility and Sterility*, vol. 72, No. 6, pp. 1073-1078 (Dec. 1999).

Liebermann et al., "Effect of carrier system on the yield of human oocytes and embryos as assessed by survival and developmental potential after vitrification", *Reproduction*, vol. 124, No. 4, pp. 483-489 (Oct. 2002).

Park et al., "Simple, efficient and succesful vitrification of bovine blastocysts using electron microscope grids", *Human Reproduction*, vol. 14, No. 11, pp. 2838-2843 (1999).

SciTech Invention—Home Page; http://scitechinvention.com/index.html; downloaded on Dec. 7, 2015.

Vanderzwalmen et al., ""In Vitro" Survival of Metaphase II Oocytes (MIII) and Blastocysts After Vitrification in a Hemi-Straw (HS) System", *Fertility & Sterility*, vol. 74, No. 3, Suppl. 1, pp. S215-S216 (Sep. 2000).

Vanderzwalmen et al., "Vitrification of human blastocysts with the Hemi-Straw carrier: application of assisted hatching after thawing", *Human Reproduction*, vol. 18, No. 7, pp. 1504-1511 (2003).

Vitrification in Assisted Reproduction, Second Edition, CRC Press, Boca Raton, FL (2016) (266 pages).

International Search Report and Written Opinion of the International Searching Authority for International Application No. PCT/US2016/053708 dated Jan. 30, 2017 (17 pages).

International Preliminary Report on Patentability and Written Opinion for International Application Serial No. PCT/US2016/053708 dated Jun. 21, 2018 (12 pages).

Japanese Office Action for Japanese Application No. JP 2018-548641 dated Aug. 27, 2019.

\* cited by examiner

LOW TEMPERATURE SPECIMEN CARRIERS AND RELATED METHODS

CROSS-REFERENCE TO RELATED APPLICATIONS

This application claims priority to U.S. Provisional Patent Application No. 62/263,894, filed on Dec. 7, 2015, and U.S. Provisional Patent Application No. 62/292,620, filed on Feb. 8, 2016, the entire contents of which are incorporated herein by reference.

TECHNICAL FIELD

This disclosure relates to low temperature specimen carriers and related methods.

BACKGROUND

Low temperature specimen carriers, such as cryopreservation devices, are used in the field of assisted reproductive technology (ART) to store and preserve living reproductive cells (e.g., oocytes, embryos, and blastocysts). Cryopreservation refers to a process where cells are preserved over extended periods of time by cooling to sub-zero temperatures. For example, a cryopreservation device can house and support cells undergoing vitrification, which is the rapid transition of a substance from a liquid phase to a solid phase (e.g., glass) without the formation of ice crystals.

Vitrifying reproductive cells using a cryopreservation device includes immersing the cells in a vitrification medium and loading the cells, suspended in a volume of the vitrification medium, onto a support member of the cryopreservation device. The support member may then be capped and plunged into a container of cooling medium (e.g., liquid nitrogen), causing the cells loaded thereon to rapidly cool to a glass state before ice crystals can form within the cells. The cryopreservation device can be stored in the cooling medium until the cells are ready to be used in reproductive procedures. At that time, the cells, which have been preserved in a viable state, can be thawed via standard warming protocols in which the cryopreservation device is removed from the cooling medium and the support member is uncapped to provide access to the cells.

SUMMARY

In general, this disclosure relates to low temperature specimen carriers that are sealable via various sealing features, such as dissimilar component materials, sealing rings, and tapered interferences, as well as related methods. Such specimen carriers can be used for preserving living specimens in a viable state over a prolonged period of time.

In one aspect, a specimen carrier includes an elongate member defining an external sealing surface and a support surface upon which a specimen can be carried, the elongate member including a first material having a first coefficient of thermal expansion. The specimen carrier further includes a cap configured to be passed over a portion of the elongate member to close a region of the cap that surrounds the specimen when the cap is passed over the portion of the elongate member, the cap defining an internal sealing surface formed complementary to the external sealing surface, and the cap including a second material having a second coefficient of thermal expansion that is greater than the first coefficient of thermal expansion, such that when the portion of the elongate member is covered with the cap and the portion of the elongate member and the cap are together placed in a cooling substance, the internal sealing surface of the cap compresses the external sealing surface of the elongate member to form a hermetic seal along an interface formed between the internal sealing surface and the external sealing surface.

Embodiments may provide one or more of the following features.

In some embodiments, the cap further defines an internal channel forming the region of the cap that surrounds the specimen when the cap is passed over the portion of the elongate member, the internal sealing surface forming a part of the internal channel.

In certain embodiments, the cap is configured to be passed over the portion of the elongate member in an ambient environment of a first temperature, and the cooling substance is of a second temperature that is lower than the first temperature.

In some embodiments, the elongate member and the cap are configured such that, at the first temperature, the interface formed between the external and internal sealing surfaces is an interference fit.

In certain embodiments, the external and internal sealing surfaces have a frustoconical shape.

In some embodiments, the first and second coefficients of thermal expansion are independent of a dimensional unit of the first and second materials, respectively.

In certain embodiments, the first material is a transparent or translucent material.

In some embodiments, the hermetic seal prevents organisms and particulates as small as about 45 nm from entering the region of the cap that surrounds the specimen when the cap is passed over the portion of the elongate member and the portion of the elongate member and the cap are together disposed in the cooling substance.

In certain embodiments, the elongate member includes a shaft configured for handling of the elongate member.

In some embodiments, the shaft includes multiple surface facets.

In certain embodiments, the shaft defines a recess that provides a tactile feedback to a user of the specimen carrier.

In some embodiments, the cap includes a rounded end that provides a tactile feedback to a user of the specimen carrier.

In certain embodiments, the elongate member defines a vertical wall that shields the support surface.

In some embodiments, the specimen includes one or more reproductive cells.

In certain embodiments, the cooling substance is a vitrification medium.

In some embodiments, the cooling substance is liquid nitrogen.

In certain embodiments, the cap further includes a third material surrounding the second material, the third material having a third coefficient of thermal expansion that is greater than the second coefficient of thermal expansion.

In some embodiments, the second and third materials together provide an aggregate coefficient of thermal expansion that is greater than the second coefficient of thermal expansion and less than the third coefficient of thermal expansion.

In certain embodiments, the specimen carrier is configured to preserve the specimen in a viable state within the cooling substance over a period of at least 40 years.

In another aspect, a method of preserving a specimen includes depositing the specimen on a support surface of an elongate member, the elongate member defining an external sealing surface. The method further includes passing a cap over a portion of the elongate member to close a region of the cap surrounding the specimen, the cap defining an internal sealing surface formed complimentary to the external sealing surface of the elongate member. The method further includes forming an interface between the external sealing surface of the elongate member and the internal sealing surface of the cap, and placing the portion of the elongate member, together with the specimen and the cap, in a cooling substance such that the internal sealing surface of the cap compresses the external sealing surface of the elongate member along the interface formed between the external sealing surface and the internal sealing surface.

Embodiments may provide one or more of the following features.

In some embodiments, the elongate member includes a first material having a first coefficient of thermal expansion, and the cap includes a second material having a second coefficient of thermal expansion that is greater than the first coefficient of thermal expansion.

In certain embodiments, the first and second coefficients of thermal expansion are independent of a dimensional unit of the first and second materials, respectively.

In some embodiments, the cap further defines an internal channel forming the region of the cap that surrounds the specimen when the cap is passed over the portion of the elongate member, the internal sealing surface forming a part of the internal channel.

In certain embodiments, the method further includes passing the cap over the portion of the elongate member in an ambient environment of a first temperature, wherein the cooling substance is of a second temperature that is lower than the first temperature.

In some embodiments, at the first temperature, the interface formed between the external and internal sealing surfaces is an interference fit.

In certain embodiments, a seal formed along the interface formed between the external sealing surface and the internal sealing surface is adapted to prevent organisms and particulates as small as about 45 nm from entering the region of the cap that surrounds the specimen when the cap is passed over the portion of the elongate member and when the portion of the elongate member and the cap are together disposed within the cooling substance.

In some embodiments, the specimen includes one or more reproductive cells.

In certain embodiments, the cooling substance is a vitrification medium.

In some embodiments, the cooling substance is liquid nitrogen.

In certain embodiments, the method further includes storing the specimen, enclosed within the region of the cap, in the cooling substance for at least 40 years.

In another aspect, a specimen carrier includes an elongate member defining an external sealing surface and a support surface upon which a specimen can be carried and a cap configured to be passed over the external sealing surface of the elongate member to close a region of the cap that surrounds the specimen when the cap is passed over the external sealing surface, wherein the cap defines an internal sealing surface sized to receive the external sealing surface of the elongate member, wherein the cap includes a sealing feature positioned along the internal sealing surface and spaced apart from an open end of the cap, the sealing feature configured to engage the external sealing surface of the elongate member to provide a hermetic seal between the cap and the elongate member when the cap is passed over the external sealing surface, and wherein the cap includes a retention feature positioned along the internal sealing surface and configured to engage the external sealing surface of the elongate member to retain the cap on the elongate member.

In some embodiments, the sealing feature is a circumferential ring.

In certain embodiments, the sealing feature is a tapered wall.

In some embodiments, the hermetic seal is provided by an interference fit between the sealing feature and the external sealing surface.

In certain embodiments, the retention feature is a circumferential ring.

In some embodiments, the retention feature is a tapered wall.

In certain embodiments, a portion of the tapered wall is configured to collapse against an associated retention feature positioned along the external sealing surface of the elongate member when external sealing surface is covered with the cap and the elongate member and the cap are together placed in a cooling substance.

In some embodiments, the associated retention feature is a circumferential relief.

In certain embodiments, the cap further includes an additional sealing feature positioned along the portion of the tapered wall, the additional sealing feature configured to engage the external sealing surface of the elongate member to provide an additional seal between the cap and the elongate member when the elongate member and the cap are together placed in the cooling substance.

In some embodiments, the additional sealing feature is a circumferential ring configured to provide a tactile feedback and/or an audible feedback as the additional sealing feature of the cap is passed over a tapered portion of the external sealing surface.

In certain embodiments, the retention feature is a recess configured to receive a complementary retention feature positioned along the external sealing surface of the elongate member when the cap is passed over the external sealing surface.

In some embodiments, the complementary retention feature is a circumferential ring.

In certain embodiments, the sealing feature and the retention feature are the same feature.

In some embodiments, at least a portion of the external sealing surface includes a tapered wall.

In certain embodiments, the cap defines a circumferential relief along the internal sealing surface and extending from the open end of the cap.

In some embodiments, the cap defines a circumferential relief along a central portion of the internal sealing surface.

In certain embodiments, the external sealing surface defines a circumferential step configured to form a gap defined by the circumferential step and the circumferential relief when the cap is passed over the external sealing surface.

In some embodiments, the elongate member includes a first material having a first coefficient of thermal expansion, and the cap includes a second material having a second coefficient of thermal expansion that is greater than the first coefficient of thermal expansion, such that when the external sealing surface is covered with the cap and the elongate member and the cap are together placed in a cooling substance, the internal sealing surface of the cap compresses the external sealing surface of the elongate member to tighten the hermetic seal between the cap and the elongate member.

In certain embodiments, the cap is configured to be passed over the external sealing surface in an ambient environment of a first temperature, and the cooling substance is of a second temperature that is lower than the first temperature.

In some embodiments, the cap further includes a third material surrounding the second material, the third material having a third coefficient of thermal expansion that is greater than the second coefficient of thermal expansion.

In certain embodiments, the second and third materials together provide an aggregate coefficient of thermal expansion that is greater than the second coefficient of thermal expansion and less than the third coefficient of thermal expansion.

In some embodiments, the hermetic seal prevents organisms and particulates as small as about 45 nm from entering the region of the cap that surrounds the specimen when the cap is passed over the external sealing surface of the elongate member.

In certain embodiments, the elongate member includes a shaft configured for handling of the elongate member.

In some embodiments, the shaft includes multiple surface facets.

In certain embodiments, the specimen includes one or more reproductive cells.

In some embodiments, the cooling substance is a vitrification medium.

In certain embodiments, the cooling substance is liquid nitrogen.

In some embodiments, the specimen carrier is configured to preserve the specimen in a viable state within the cooling substance over a period of at least 40 years.

In certain embodiments, the cap includes a rounded end that provides a tactile feedback to a user of the specimen carrier.

In some embodiments, the elongate member defines a vertical wall that shields the support surface.

In some embodiments, the sealing feature is spaced apart from the open end of the cap by at least about 0.5 mm.

In certain embodiments, the sealing feature is spaced apart from the open end of the cap by about 0.5 mm to about 7.0 mm.

In another aspect, a method of preserving a specimen includes depositing the specimen on a support surface of an elongate member and passing an internal sealing surface of a cap over an external sealing surface of the elongate member to close a region of the cap surrounding the specimen. The method further includes forming a hermetic seal between a sealing feature positioned along the external sealing surface of the elongate member and the internal sealing surface of the cap, the sealing feature being spaced apart from an open end of the cap. The method further includes retaining the cap on the external sealing surface of the elongate member with a retention feature positioned along the internal sealing surface of the cap.

In some embodiments, the sealing feature is a circumferential ring.

In certain embodiments, the sealing feature is a tapered wall.

In some embodiments, the method further includes forming an interference fit between the sealing feature and the external sealing surface.

In certain embodiments, the retention feature is a circumferential ring.

In some embodiments, the retention feature is a tapered wall.

In certain embodiments, the method further includes collapsing a portion of the tapered wall against an associated retention feature positioned along the external sealing surface of the elongate member when the elongate member and the cap are together placed in a cooling substance.

In some embodiments, the method further includes forming an additional seal between an additional sealing feature positioned along the portion of the tapered wall and the external sealing surface of the elongate member when the elongate member and the cap are together placed in the cooling substance.

In certain embodiments, the additional sealing feature is a circumferential ring configured to provide a tactile feedback and an audible feedback as the additional sealing feature of the cap is passed over a tapered portion of the external sealing surface.

In some embodiments, the retention feature is a recess configured to receive a complementary retention feature positioned along the external sealing surface of the elongate member when the cap is passed over the external sealing surface.

In certain embodiments, the complementary retention feature is a circumferential ring.

In some embodiments, the sealing feature and the retention feature are the same feature.

In certain embodiments, the method further includes placing the elongate member, together with the specimen and the cap, in a cooling substance.

In some embodiments, the elongate member includes a first material having a first coefficient of thermal expansion, and the cap includes a second material having a second coefficient of thermal expansion that is greater than the first coefficient of thermal expansion, such that the internal sealing surface of the cap compresses the external sealing surface of the elongate member when the elongate member and the cap are together placed in the cooling substance.

In certain embodiments, the cap further includes a third material surrounding the second material, the third material having a third coefficient of thermal expansion that is greater than the second coefficient of thermal expansion, such that the second and third materials together provide an aggregate coefficient of thermal expansion that is greater than the second coefficient of thermal expansion and less than the third coefficient of thermal expansion.

In some embodiments, the method further includes passing the cap over the external sealing surface of the elongate member in an ambient environment of a first temperature, wherein the cooling substance is of a second temperature that is lower than the first temperature.

In certain embodiments, the cooling substance is a vitrification medium.

In some embodiments, the cooling substance is liquid nitrogen.

In certain embodiments, the method further includes storing the specimen, enclosed within the region of the cap, in the cooling substance for at least 40 years.

In some embodiments, the specimen includes one or more reproductive cells.

In some embodiments, the sealing feature is spaced apart from the open end of the cap by at least about 0.5 mm.

In certain embodiments, the sealing feature is spaced apart from the open end of the cap by about 0.5 mm to about 7.0 mm.

Embodiments may provide one or more of the following advantages.

In some embodiments, with the elongate member in a capped state while submerged in the cooling substance, the internal sealing surface of the cap shrinks against the external sealing surface of the elongate member, thereby increasing the extent of closure (e.g., tightness) of the region the cap to form a tight, intimate fit (or, in some cases, a tighter intimate fit) along the interface, such that the hermetic seal (e.g., an airtight seal) is formed at the interface between the external and internal sealing surfaces. The hermeticity of the seal is sufficient to prevent particulates and organisms (e.g., the HIV or Hepatitis B viruses) of sizes as small as about 45 nm from penetrating the seal and therefore preventing the particulates and organisms from entering the region of the cap and from contaminating the specimen contained therein. The seal provided along the interface has a greater hermeticity than would otherwise be achieved for an equivalently dimensioned interfacing cap and elongate member formed of the same material. The hermetic seal along the interface remains intact as long as the specimen carrier remains submerged within the cooling substance.

In some embodiments, when a specimen carrier including a cap with an internal sealing feature (e.g., one or more circumferential sealing rings or a tapered wall) is pressed onto the tip of a stick member, the interference fit formed along an interface between the sealing feature of the cap and the external sealing surface of the tip causes the cap to expand slightly in the region of the internal sealing feature, such that the cap experiences localized frictional forces in the region without stretching of the entire cap. Providing the internal sealing feature at a sufficient distance away from the open end of the cap advantageously avoids stress-induced fractures that may otherwise result if such a sealing feature was located closer to the open end of such a cap. Furthermore, the interference fit formed along the interface may provide a dual functionality of hermetic sealing that prevents contamination of the internal channel of the cap and retention of the cap on the stick member.

In some embodiments, serial placement of one sealing ring forward of one or more additional sealing rings along the internal channel of the cap provides one or more additional degrees of sealing that can prevent passage of particulates and organisms that manage to penetrate rearward sealing rings. In some embodiments, as the elasticity of the material from which the sealing rings is made increases, the elastic deformation that occurs upon pressing the cap onto the tip increases, providing more friction at the interfaces formed at the sealing rings, tighter seals, and improved retention of the cap on the stick member.

In some embodiments, a specimen carrier advantageously includes a sealing structure (e.g., a tapered wall-to-wall interface) and a retention feature (e.g., a snap ring and an associated recess) that are isolated from each other. In such embodiments, an interference fit formed between a tapered wall of the cap and the tip of the stick member provides a hermetic seal that prevents contamination of the internal channel of the cap, while a snap ring on the tip of the stick member and a recess within the tapered wall of the cap together provide a securement feature that retains the cap on the stick member. Furthermore, when the cap is passed over the tip, seating of the snap ring within the recess with can provide a tactile feedback and/or an audible feedback to a user indicating that the cap is properly secured to the stick member.

In some embodiments, a specimen carrier may include a relief area on a tip of the stick member that provides a retention capability. For example, in some embodiments, the external sealing surface of a tip of the stick member may define a circumferential relief positioned rearward of a tapered portion of the external sealing surface, and a tapered wall of the associated cap is formed to interfere with the tapered portion of the external sealing surface when the cap is passed fully over the tip. When the specimen carrier is immersed in the low temperature substance, the rear portion of the tapered wall of the cap relaxes (e.g., collapses) into a gap formed between the circumferential relief of the tip and the wall of the cap to retain the cap on the stick member. Thus, the rear portion of the tapered wall and the circumferential relief together provide a securement feature that further retains the cap on the stick member, while the interference fit between a forward portion of the tapered wall of the cap and the tip provides a hermetic seal that prevents contamination of the internal channel of the cap.

In some embodiments, a specimen carrier includes both a cap with sealing rings and a stick member with a relief area. When the cap of such a specimen carrier is passed over the tip of the stick member, the sealing ring provides a tactile feedback and/or an audible feedback to a user as the sealing ring passes along the tapered portion of the external sealing surface of the tip into a rearward relief formed on the external sealing surface. The feedbacks indicate to the user that the cap has been passed over the tip of the stick member by at least a minimum distance. A rear portion of the wall of the cap and the rearward relief of the tip together provide a securement feature that retains the cap on the stick member. That is, when the specimen carrier is immersed in the low temperature substance, the rear portion of the wall of the cap relaxes (e.g., collapses) into the gap formed by the relief to retain the cap on the stick member.

In some embodiments, a relief extending inwardly from the open end of the cap of the specimen carrier serves to avoid generation of excessive frictional forces that may otherwise result between the cap and the tip, thereby reducing the generation or propagation of any resulting stress fractures in the cap near the open end. In some embodiments, the cap defines a relief positioned along a central portion of the wall of the cap that alleviates forward frictional forces formed between the wall of the cap and the external sealing surface of the tip of the stick member.

For embodiments in which the coefficient of thermal expansion (CTE) of one or more materials from which the cap is made is greater than the CTE of the material from which the tip is made, the sealing structure of the cap (e.g., one or more sealing rings or a tapered wall) moves with respect to (e.g., shrinks against) the external sealing surface of the tip such that the interfaces become dynamic upon submersion in the low temperature substance. In this manner, the sealing provided by the interference fits formed at the interfaces may be tightened even further due to thermal affects. In some embodiments, the wall of the cap may include two or more layers made of different, respective materials providing an aggregate CTE that is greater than the CTE of the material from which the tip is made. In such embodiments, one or more outer layers of the cap may enforce the behavior of one or more inner layers of the cap relative to the tip, thereby providing a tighter closure between the external sealing surface of the tip and an inner-most layer of the wall of the cap.

Other aspects, features, and advantages will be apparent from the description, the drawings, and the claims.

DETAILED DESCRIPTION

Figure 1:
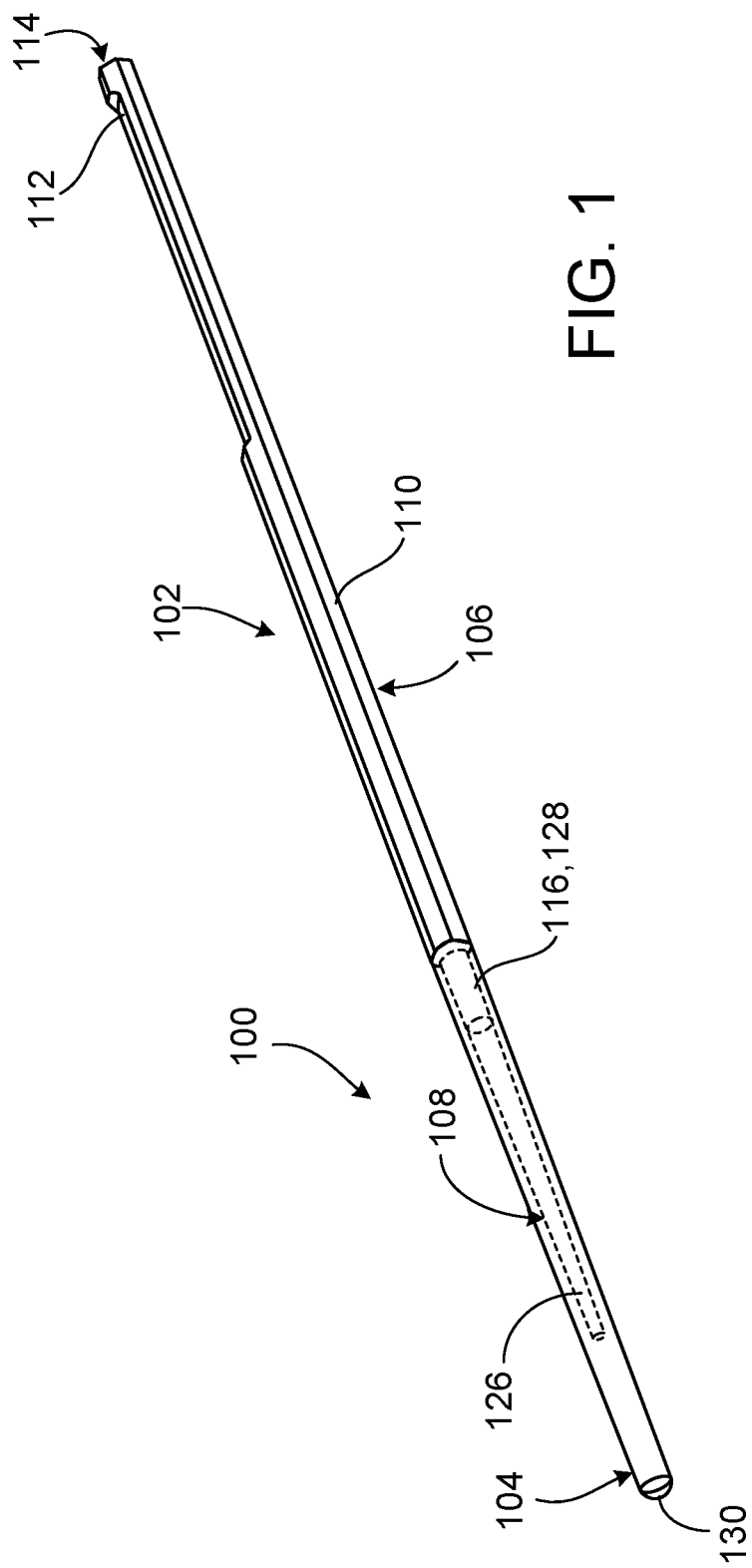
FIG. 1 is a perspective view of a specimen carrier in a capped state.

FIG. 1 illustrates a specimen carrier 100 adapted for submersion and storage in a low temperature substance. The specimen carrier 100 is a cryopreservation device that is configured to house and store a variety of specimens (e.g., cellular samples and tissue samples) in a viable and vitrified state within the low temperature substance until the specimens are desired for use (e.g., over a period of up to about 40 years). The specimens may include reproductive specimens, such as oocytes, embryos (e.g., cleavage stage embryos), and blastocysts, or other samples, such as T-cells. Such specimens may be mammalian samples or non-mammalian samples. The low temperature substance (e.g., liquid nitrogen or cryogenic plasma) maintains the specimens in a vitrified state and has a temperature of about −80° C. to about −200° C. (e.g., about −196° C.).

Figure 2:
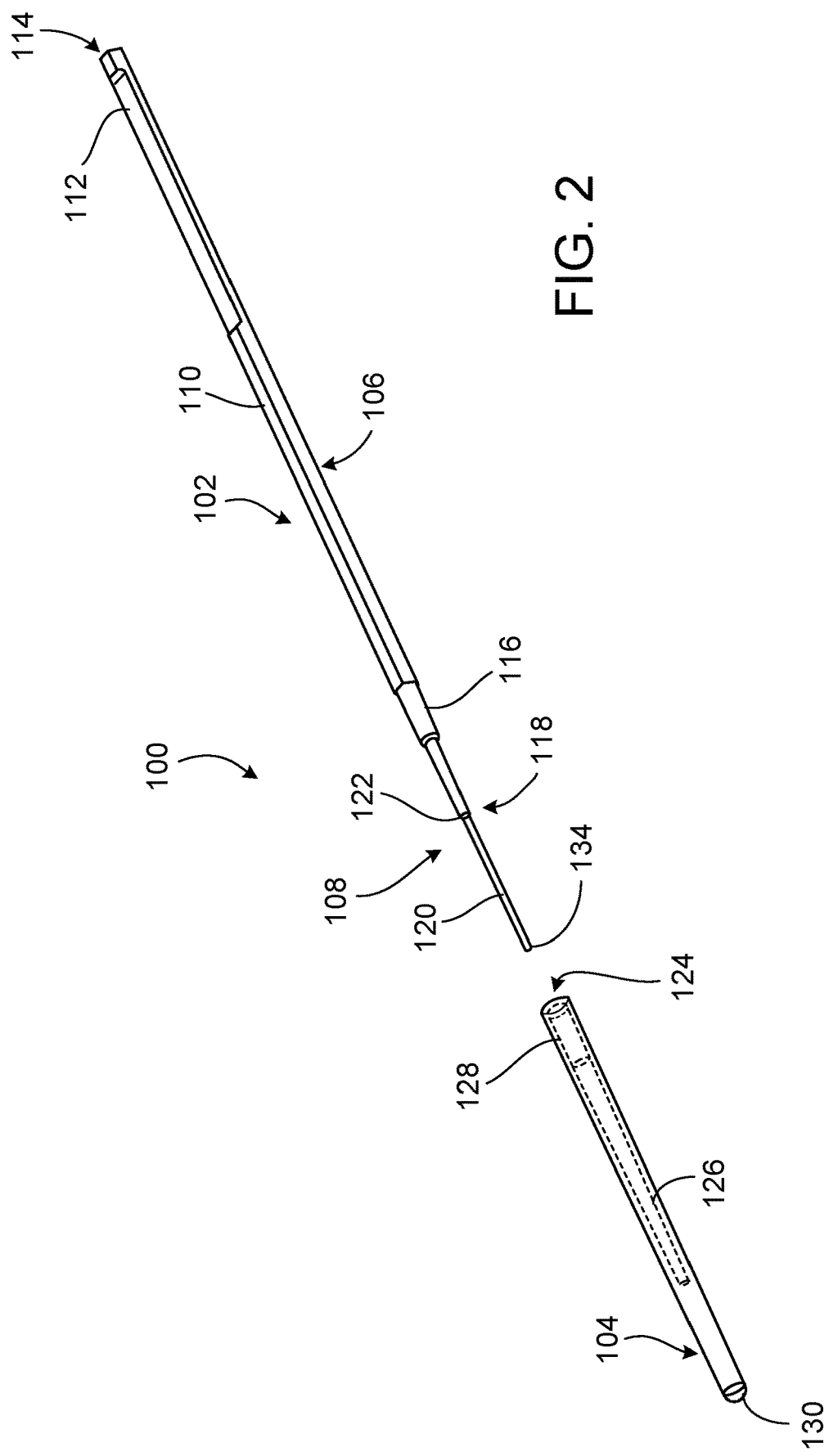
FIG. 2 is a perspective view of the specimen carrier of FIG. 1 in an uncapped state.

Referring to FIGS. 1 and 2, the specimen carrier 100 includes a stick member 102 (shown in a capped state and an uncapped state, respectively) and a cap 104 that can be passed over a portion of the stick member 102. The stick member 102 includes a shaft 106 by which the stick 102 can be handled and a tip 108 extending from the shaft 106.

The shaft 106 has a surface defined by hexagonal facets 110 that prevent the stick member 102 from rolling on a surface. Accordingly, the shaft 106 has a hexagonal cross-sectional shape. The shaft 106 defines a flat, elongate recess 112 that provides tactile feedback indicating that the specimen carrier 100 is being handled at the appropriate end of the specimen carrier 100. The recess 112 further provides a visual indication that the specimen carrier 100 is oriented correctly while the specimen carrier 100 is being submerged in the low temperature substance or removed from a storage container. The recess 112 also provides a surface on which information (e.g., patient identification information, specimen identification information, a date, or other information) can be written or otherwise printed. A texture (e.g., a light frosting or a matt finish) of the surface of the recess 112 facilitates writing and printing, legibility of writing and printing, and retention of ink on the recess 112. Markings may also be printed on a surface of an end portion 114 of the shaft 106. Such markings may indicate information such as patient identification information, specimen identification information, a date, or other information. The shaft 106 typically has a length of about 40 mm to about 200 mm (e.g., about 130 mm) and a maximum width of about 2.5 mm to about 6 mm (e.g., about 2.7 mm). The shaft 106 may be manufactured via an injection molding process or a casting process. The shaft 106 is made of one or more materials that can withstand the low temperature substance, including but not limited to polymers such as polystyrene, polypropylene, polyvinyl acetate, and polycarbonate.

Figure 3:
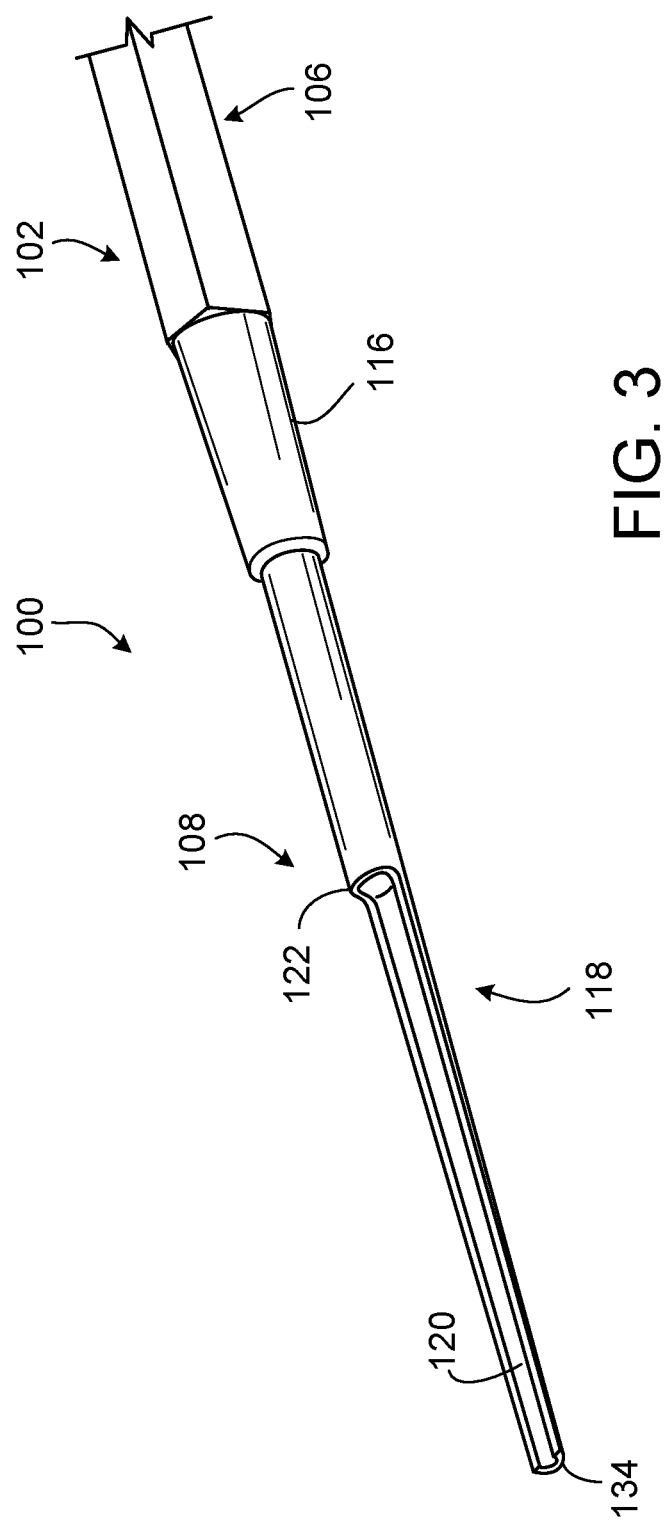
FIG. 3 is an enlarged, perspective view of a tip of the specimen carrier of FIG. 1.

FIG. 3 illustrates an enlarged view of the tip 108 of the stick member 102. The tip 108 is formed as a generally conical member that may be slid into the cap 104 (e.g., at an ambient temperature) to form an interface between the tip 108 and the cap 104. The tip 108 defines an external sealing surface 116 configured to form the interface with the cap 104 and a tip extension 118 that extends from the external sealing surface 116. The external sealing surface 116 has a generally frustoconical shape. The tip extension 118 defines a loading surface 120 (e.g., a support surface) upon which a specimen can be deposited and a vertical wall 122 that protects (e.g., shields) the loading surface 120. The loading surface 120 is formed as a concave surface that extends from the vertical wall 122 to an end 134 of the tip 108. The loading surface 120 is sized to hold one or two cells (e.g., reproductive cells). The tip 108 is also transparent or translucent to allow easy viewing of the cells under a microscope while the cells are supported on the loading surface 120.

The loading surface 120 of the tip 108 typically has a length of about 2 mm to about 20 mm (e.g., about 16.5 mm) and a width of about 0.5 mm to about 2 mm (e.g., about 1.1 mm), allowing for easy placement of the cells, which typically have widths ranging from about 0.05 mm to about 0.16 mm. A thickness of the loading surface 120 is designed to allow maximum cell cooling rates when the specimen carrier 100 is submerged in the low temperature substance and maximum warming rates when the specimen carrier 100 is removed from the low temperature substance. The external sealing surface 116 of the tip 108 typically has a length of about 4 mm to about 10 mm (e.g., about 6.5 mm), a maximum diameter of about 1.5 mm to about 5 mm (e.g., about 2.2 mm), and a minimum diameter of about 1.5 mm to about 5 mm (e.g., about 2.0 mm). The tip 108 typically has a total length of about 25 mm to about 50 mm (e.g., about 30 mm). The tip 108 may be manufactured via a casting process or via an injection molding process (e.g., via a single injection molding process in which both the shaft 106 and the tip 108 are manufactured as an integral component or via a separate injection molding process, following which the tip 108 is subsequently joined to the shaft 106 as a subcomponent of the stick member 102). The tip 108 is made of one or more materials that can withstand the low temperature substance, including but not limited to polymers such as polystyrene, polypropylene, polyvinyl acetate, and polycarbonate. In some embodiments, the one or more materials are translucent or transparent. The tip 108 and the shaft 106 may be made of the same material or made of different materials, depending on the process used to manufacture the tip 108 and the shaft 106.

Referring again to FIGS. 1 and 2, the cap 104 is sized to be passed over the tip 108 to form an interface between the tip 108 and the cap 104. The cap 104 forms a generally conical shaped internal channel 124 defined by an internal surface 126. The internal surface 126 includes an internal sealing surface 128 configured to interface with the external sealing surface 116 of the tip 108. Accordingly, the internal sealing surface 128 has a generally frustoconical shape. A rounded end 130 of the cap 104 provides a tactile feedback that tactilely differentiates the cap 104 from the stick member 102. The internal sealing surface 128 of the cap 104 typically has a length, a maximum diameter, and a minimum diameter that are about equal to the length, the maximum diameter, and the minimum diameter, respectively, of the external sealing surface 116 of the tip 108. In some embodiments, the internal sealing surface 128 has a length that is longer than the length of the external sealing surface 116, a maximum diameter that is larger than the maximum diameter of the external sealing surface 116, and a minimum diameter that is smaller than the minimum diameter of the external sealing surface 116. The internal channel 124 of the cap 104 has a length that is about equal to the length of the tip 108 of the stick member 102, a maximum diameter that is about equal to the maximum diameter of the external and internal sealing surfaces 116, 128, and a minimum diameter of about 1 mm to about 4 mm (e.g., about 1 mm). The cap 104 typically has a total length of about 25 mm to about 55 mm (e.g., about 45 mm).

As discussed above, the cap 104 may be passed over the tip 108 (e.g., loaded with a specimen) at room temperature to provide the interface between the internal sealing surface 128 of the cap 104 and the external sealing surface 116 of the tip 108. Depending on the extent to which the cap 104 is passed over the tip 108, and according to a tapered geometry of the cap 104 and the tip 108, the interface may provide different levels of closure. For example, when the cap 104 is passed over the tip 108 to the extent that a distal end of the internal sealing surface 128 remains distal to a distal end of the external sealing surface 116, the interface provides a clearance (e.g., a small gap) between the external and internal sealing surfaces 116, 128 along an area in which the external and internal sealing surfaces 116, 128 overlap. When the cap 104 is passed over the tip 108 to the extent that corresponding ends of the external and internal sealing surfaces 116, 128 are substantially aligned, the interface provides an interference fit (e.g., a mild press fit) that frictionally, releasably secures the cap 104 to the stick member 102. In some examples, the cap 104 is passed over the tip 108 to the extent that the distal end of the internal sealing surface 128 is proximal to the distal end of the external sealing surface 116, thereby providing an intimate fit (e.g., a strong press fit) that frictionally, releasably, secures the cap 104 to stick member 102 along an area in which the external and internal sealing surfaces 116, 128 overlap.

When the temperature of the specimen carrier 100 changes (e.g., when the specimen carrier 100 is heated or cooled), each component of the specimen carrier 100 undergoes a dimensional change by an amount that is proportional to the original dimension of the component and to the change in temperature. For example, when the specimen carrier 100 is cooled (e.g., submerged in the low temperature substance), the cap 104 and the stick member 102 contract (e.g., shrink), whereas when the specimen carrier 100 is heated (e.g., allowed to thaw upon removal from the low temperature substance), the cap 104 and the stick member 102 expand. This effect can be described by a coefficient of thermal expansion (CTE), which defines how the size of an object changes with a change in temperature. The CTE is defined as the ratio of a fractional change in one or more dimensions per unit (e.g., degree) change in temperature at a constant pressure, as provided in EQU. 1, where a is the CTE, D is the original length (for the case of a one-dimensional length CTE), the original area (for the case of a two-dimensional area CTE), or the original volume (for the case of a three-dimensional volumetric CTE); AD is the change in D, 4T is the change in the temperature, and p denotes a constant pressure.

$$\alpha = \frac{1}{D}\left(\frac{\Delta D}{\Delta T}\right)_p \quad (1)$$

In some cases, the CTE of a material varies as a function of the absolute temperature. However, the CTE is often assumed to be a constant value for the purpose of simplifying analyses.

Figure 4:
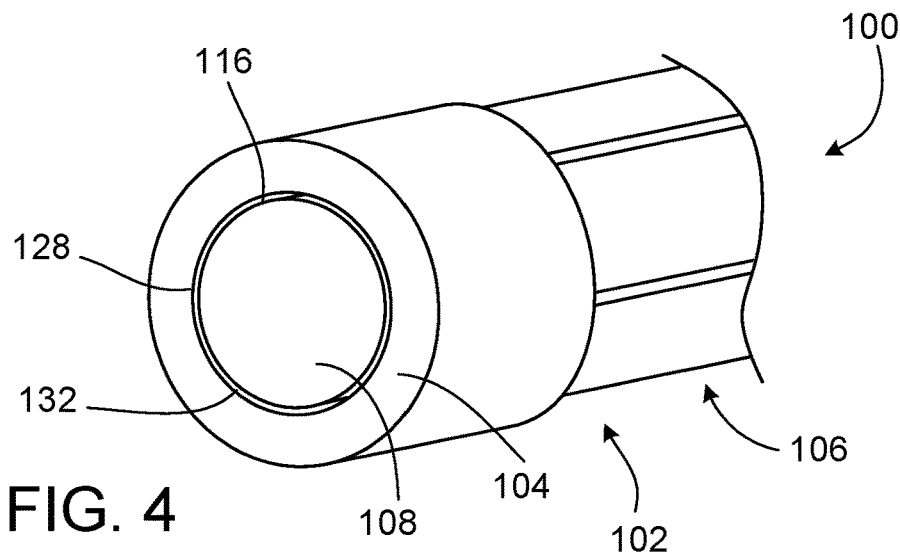
FIG. 4 is a cross-sectional perspective view of the specimen carrier of FIG. 1 with a stick of the specimen carrier in the capped state at a relatively high temperature.

FIG. 4 illustrates a cross-sectional perspective view of the specimen carrier 100 with the stick 102 in the capped state at a relatively high temperature (e.g., a room temperature of about 25° C.). At the relatively high temperature, the cap 104 is typically passed over the stick 102 to the extent that an interface 132 between the external and internal sealing surfaces 116, 128 provides an interference fit, as described above. The cap 104 is made of a material that has a CTE that is greater than a CTE of the material from which the tip 108 is made, such that when the specimen carrier 100 is submerged in the low temperature substance (e.g., liquid nitrogen at a temperature of about −196° C.), the cap 104 contracts to a greater extent per degree temperature change (e.g., at a faster rate) than does the tip 108, causing the internal sealing surface 128 of the cap 104 to shrink against (e.g., compress) the external sealing surface 116 of the tip 108. For the example specimen carrier 100, the materials from which the cap 104 and the tip 108 are made behave substantially the same in all three dimensions with respect to thermal expansion, such that the cap 104 and the tip 108 can be described with respect to CTEs that are independent of a dimensional unit (e.g., length, area, or volume) of the respective materials. In some embodiments, the CTE of the material from which the cap 104 is made is about $[100\times10^{-6}]/°$ C. to about $[200\times10^{-6}]/°$ C. (e.g., about $[150\times10^{-6}]/°$ C.), and the CTE of the material from which the tip 108 is made is about $[50\times10^{-6}]/°$ C. to about $[80\times10^{-6}]/°$ C. (e.g., about $[70\times10^{-6}]/°$ C.).

Figure 5:
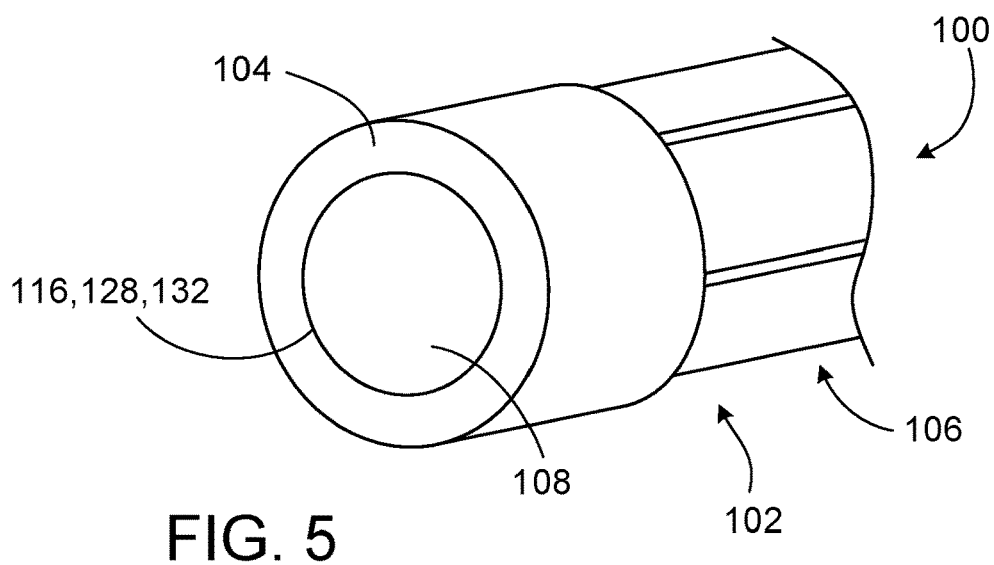
FIG. 5 is a cross-sectional view of the specimen carrier of FIG. 1 with the stick of the specimen carrier in the capped state while submerged in a low temperature substance.

FIG. 5 illustrates a cross-sectional view of the specimen carrier 100 with the stick 102 in the capped state while submerged in the low temperature substance. Within the low temperature substance, the internal sealing surface 128 of the cap 104 shrinks against the external sealing surface 116 of the tip 108, thereby increasing the extent of closure (e.g., tightness) to form a tight, intimate fit (or, in some cases, a tighter intimate fit) along the interface 132, such that a hermetic seal (e.g., an airtight seal) is formed at the interface 132 between the external and internal sealing surfaces 116, 128. The hermeticity of the seal (e.g., the extent to which the seal is able to prevent air from penetrating the seal) is sufficient to prevent particulates and organisms (e.g., the HIV and Hepatitis B viruses) of sizes as small as about 45 nm from penetrating the seal and therefore preventing the particulates and organisms from entering the internal channel 124 of the cap 104 and from contaminating the specimen contained therein. In some examples, the seal is defined as hermetic at an air leak rate of less than $10^{-5}$ atm-cc/sec. The seal provided along the interface 132 has a greater hermeticity as compared to a specimen carrier including a tip and a cap of the same geometries as the tip 108 and the cap 104 and formed of the same material. The hermetic seal along the interface 132 remains intact as long as the specimen carrier 100 remains submerged within the low temperature substance.

Upon removal of the specimen carrier 100 from the low temperature substance (e.g., in order to use the specimen in a reproductive procedure), the components of the specimen carrier 100 will stress relax over time. Accordingly, the cap 104 and the tip 108 will expand such that the interface 132 between the external and internal sealing surfaces 116, 128 loosens, thereby reducing the level of closure of the internal channel 124 and releasing the hermetic seal.

The specimen carrier 100 is a sterile, single-use device that is non-toxic to cellular and tissue specimens. The specimen carrier 100 may be individually packaged, and both the specimen carrier 100 and the packaging will remain sterile for a guaranteed shelf-life of the specimen carrier 100. The specimen carrier 100 typically has a total length (e.g., in a capped state) of about 12 cm to about 14 cm (e.g., about 13 cm), which allows the specimen carrier 100 to fit within standard storage containers and other standard equipment used in ART protocols.

In order to vitrify reproductive cells using the specimen carrier 100, the cells are first immersed in an equilibrium medium and then in a vitrification medium containing high concentrations of cryoprotectants. Permeation of the cryoprotectants into the cells replaces water within the cells, thereby dehydrating the cells and increasing the intracellular viscosity of the cells. A micropipette is then used to load one or two cells, suspended in a minimally adequate volume of vitrification medium, onto the loading surface 120 of the specimen carrier 100. The stick member 102 is slid inside of the cap 104, thereby providing the interface 132 between the internal sealing surface 128 of the cap 104 and the internal sealing surface 116 of the tip 108 to close the internal channel 124 of the cap 104. In a capped state, the specimen carrier 100 is then plunged into a container of the low temperature substance (e.g., a cooling substance), causing the cells to rapidly cool to a glass state before ice crystals can form within the cells to preserve the cells in a viable state. The specimen carrier 100 can be stored in the low temperature substance until the cells are ready to be used in reproductive procedures. At such a time, the specimen carrier 100 can be removed from the low temperature substance. The cells can subsequently be thawed via standard warming protocols in which the stick member 102 of the specimen carrier 100 is uncapped and the cells are exposed to one or more warming solutions.

While certain embodiments have been described above, other embodiments are possible.

Figure 6:
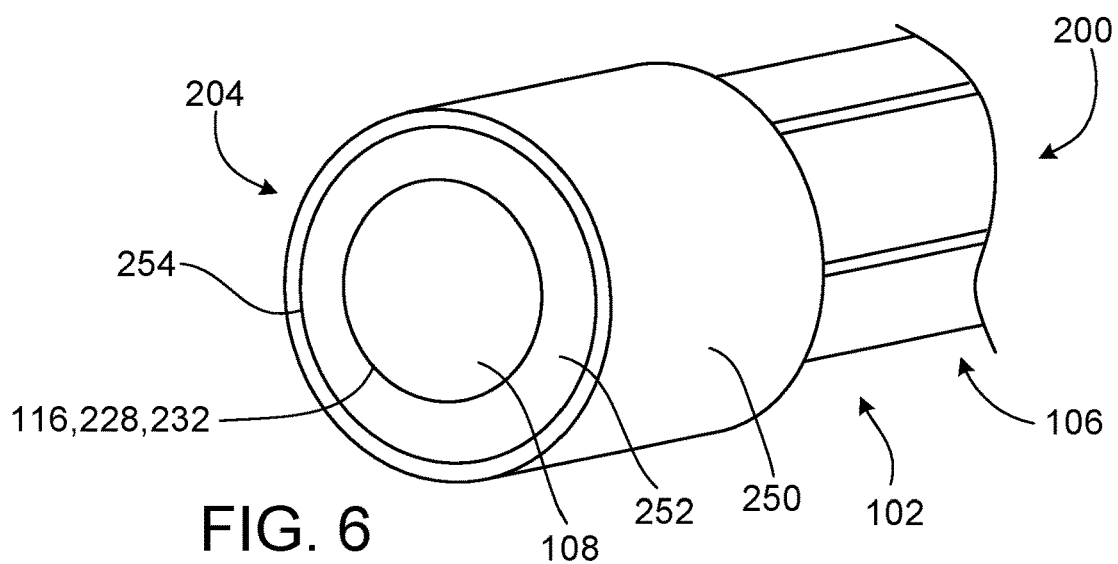
FIG. 6 is a cross-sectional perspective view of a specimen carrier including a multi-layered cap with a stick of the specimen carrier in a capped state while submerged in a low temperature substance.

For example, while the specimen carrier 100 has been described as including the cap 104 formed of one material, a specimen carrier may have a cap that is formed of two or more materials providing an aggregate CTE that is greater than a CTE of the material form which the tip is made. In some embodiments, as shown in FIG. 6, a specimen carrier 200 includes the stick member 102 and a cap 204. The cap 204 is substantially similar in size and shape to the cap 104 of the specimen carrier 100, except that the cap 204 is made of two different materials. The cap 204 includes an outer layer 250 made of a first material and an inner layer 252 made of a second material. The outer and inner layers 250, 252 may be made of one or more materials, including but not limited to polymers (e.g., polystyrene, polypropylene, polyvinyl acetate, polycarbonate, and polysulfone), composite materials, ceramics, and metals (e.g. steel or titanium).

The inner layer 252 has an internal sealing surface 228 (e.g., of substantially the same size and shape of the internal sealing surface 128 of the cap 104) that forms an interface 232 with the external sealing surface 116 of the tip 108 when the cap 204 is passed over the tip 108. The first material of the outer layer 250 has a CTE that is greater than a CTE of the second material from which the inner layer 252 is made, and the CTE of the second material is greater than the CTE of the material from which the tip 108 is made. Thus, an aggregate CTE provided by the first and second materials of the cap 204 (e.g., describing a behavior at an interface 254 between the outer and inner layers 250, 252) is greater than the CTE of the material from which the tip 108 is made.

When the specimen carrier 200 is submerged in the low temperature substance, the outer layer 250 contracts at a faster rate than does the inner layer 252, causing the outer layer 250 to shrink against (e.g., compress) the inner layer 252, and the inner layer 252 contracts at a faster rate than does the tip 108, causing the internal sealing surface 228 to shrink against (e.g., compress) the external sealing surface 116 of the tip 108. In this manner, the outer layer 250 of the cap 204 enforces the behavior of the inner layer 252 with respect to the tip 108, thereby providing a tighter closure (e.g., a seal of a greater hermeticity) between the external sealing surface 116 of the tip 108 and the internal sealing surface 228 of the inner layer 252, as compared to a seal that would otherwise form between the cap 104 and the tip 108 of the specimen carrier 100 in a case where the cap 104 is made of the same material from which the inner layer 252 of the specimen carrier 200 is formed.

Figure 7:
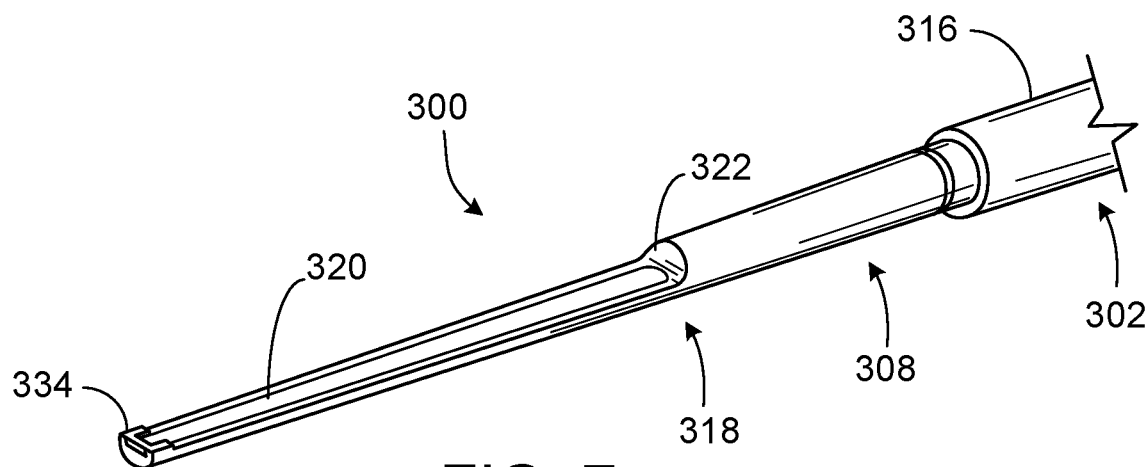
FIG. 7 is a perspective view of a specimen carrier with a tip that includes a flat, rectangular loading surface.

While the specimen carrier 100 has been described as including the tip 108 with the concave loading surface 120, in some embodiments, a specimen carrier may have a tip including feature geometries that are different from the those of the tip 108. For example, as shown in FIG. 7, a specimen carrier 300 includes a stick member 302 that has a tip 308 that is substantially similar in function and size and similar in construction to the tip 108 of the specimen carrier 100, except that the tip 308 includes a flat, rectangular loading surface. In particular, the tip 308 defines an external sealing surface 316 that is equivalent in geometry to the external sealing surface 116 of the tip 108 and a tip extension 318 that extends from the external sealing surface 316. The tip extension 318 defines a loading surface 320 upon which a specimen can be deposited and a vertical wall 322 that protects (e.g., shields) the loading surface 320. The loading surface 320 is formed as a flat channel that extends from the vertical wall 322 to an end flange 334 of the tip 308. The end flange 334 is configured to provide additional protection of the loading surface 320 and to provide a structure for supporting a pipette cannula during loading. Similar to the loading surface 120 of the tip 108, the loading surface 320 is sized to hold one or two cells. The tip 308 may be manufactured using the techniques and made of the materials as described above with respect to the tip 108 of the specimen carrier 100.

Figure 8:
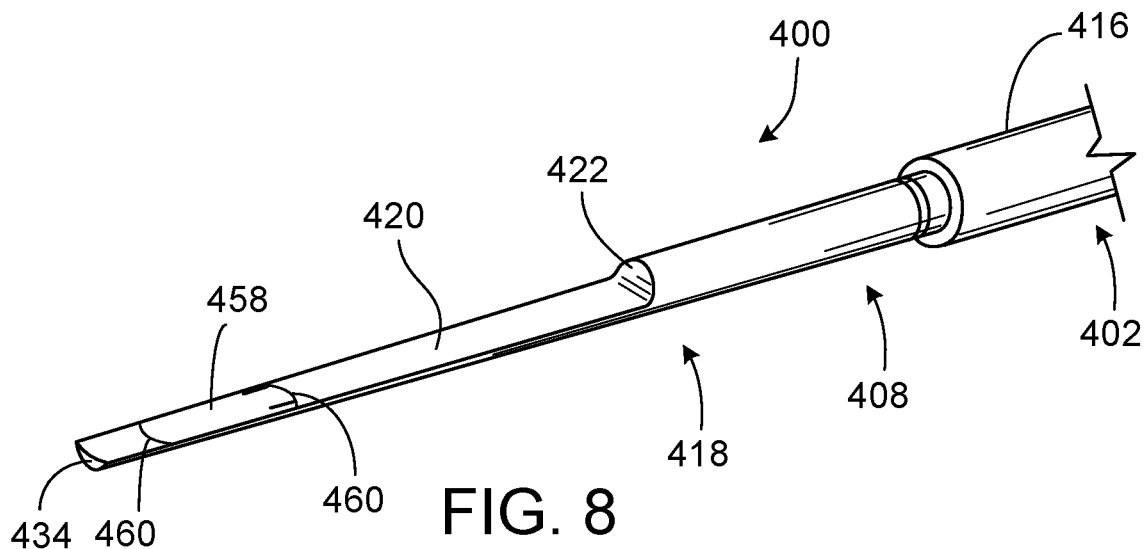
FIG. 8 is a perspective view of a specimen carrier with a tip that includes a loading surface that defines a loading platform.

In some embodiments, as shown in FIG. 8, a specimen carrier 400 includes a stick member 402 that has a tip 408 that is substantially similar in function and size and similar in construction to the tips 108, 308 of the specimen carriers 100, 300, except that the tip 408 includes a loading surface that further defines a loading platform. For example, the tip 408 defines an external sealing surface 416 that is equivalent in geometry to the external sealing surface 116 of the tip 108 and a tip extension 418 that extends from the external sealing surface 416. The tip extension 418 defines a loading surface 420 that further defines a loading platform 458 indicating where a specimen may be deposited. The loading platform 458 includes convex end regions 460. The loading platform 458 is configured to guide placement of the cells on the loading surface 420 with more locational specificity. In some embodiments, the loading platform 458 may reduce the thermal mass of the tip extension 418. In some embodiments, the loading platform 458 may also provide a region that is thinner or more light transmissive than the surrounding loading surface 420. The tip extension 418 further defines a vertical wall 422 that protects (e.g., shields) the loading surface 420. The loading surface 420 is formed as a flat, rectangular surface that extends from the vertical wall 422 to an end 434 of the tip 408. Similar to the loading surfaces 120, 320 of the tips 108, 308, the loading surface 420 is sized to hold one or two cells. The tip 408 may be manufactured using the techniques and made of the materials as described above with respect to the tip 108 of the specimen carrier 100.

Figure 9:
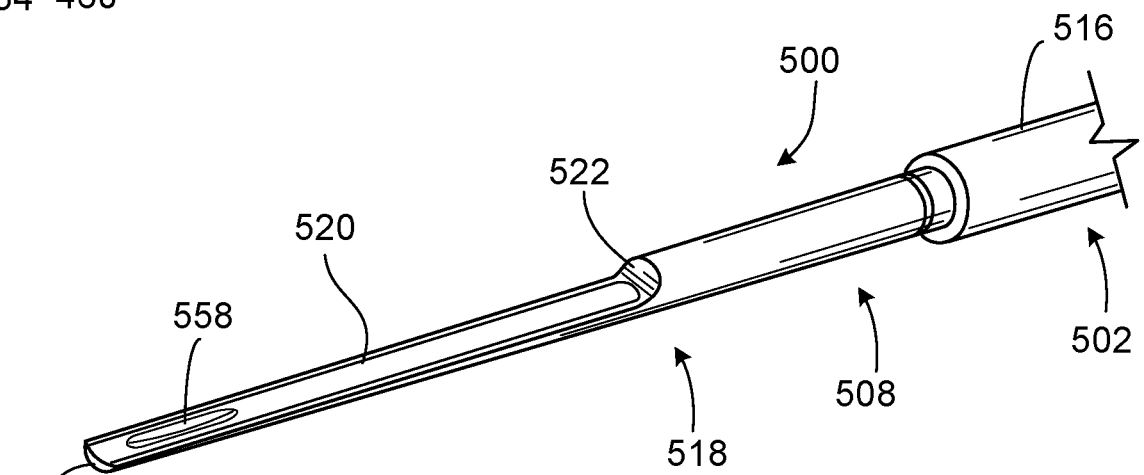
FIG. 9 is a perspective view of a specimen carrier with a tip that includes a loading pocket.

In some embodiments, as shown in FIG. 9, a specimen carrier 500 includes a stick member 502 that has a tip 508 that is substantially similar in function and size and similar in construction to the tips 108, 308, 408 of the specimen carriers 100, 300, 400 except that the tip 508 includes a loading pocket near an end of the tip 508. For example, the tip 508 defines an external sealing surface 516 that is equivalent in geometry to the external sealing surface 116 of the tip 108 and a tip extension 518 that extends from the external sealing surface 516. The tip extension 518 defines a loading surface 520 and a loading pocket 558 where a specimen may be deposited. The loading surface 520 is formed as a flat channel that extends from a vertical wall 522 to an end 534 of the tip 508. The loading pocket 558, located near the end 534 of the tip 508, is sized to hold one or two specimens that each includes one or more cells. The tip 508 may be manufactured using the techniques and made of the materials as described above with respect to the tip 108 of the specimen carrier 100.

Figure 10:
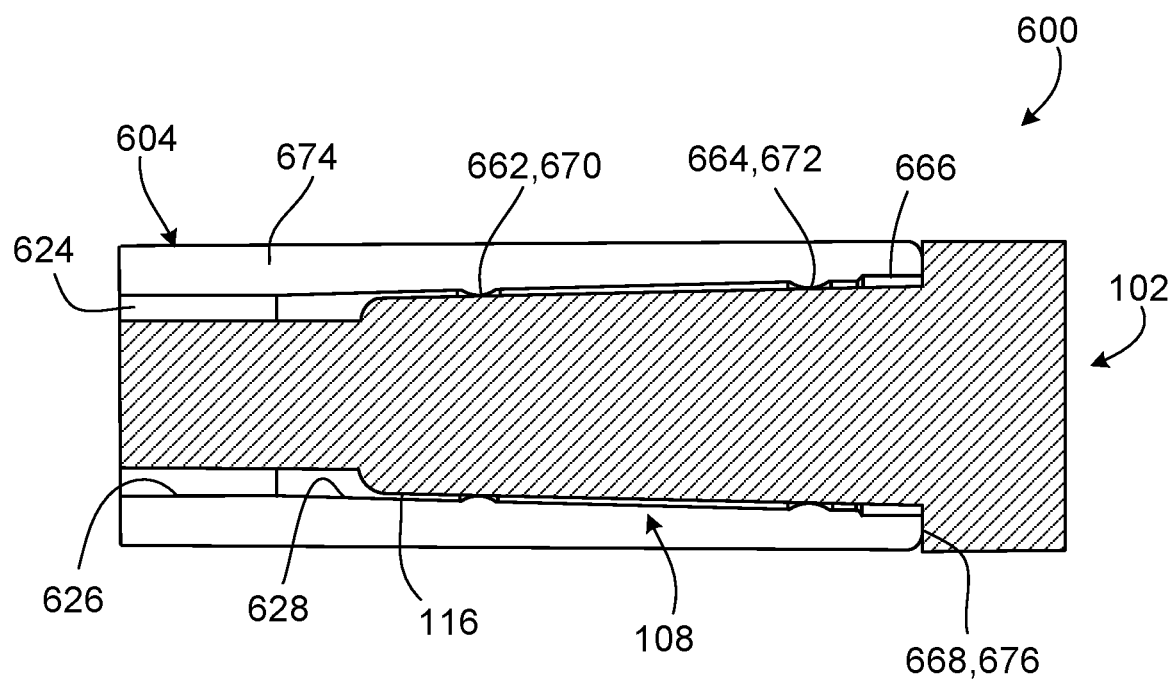
FIG. 10 is a cross-sectional view of a specimen carrier including two sealing rings, with the specimen carrier in a capped state at a relatively high temperature.

While the specimen carriers 100, 200, 300, 400, 500 have been described as being sealable via dissimilar component materials, in some embodiments, a specimen carrier may alternatively or additionally include other sealing features. For example, as shown in FIG. 10, a specimen carrier 600 includes circumferential sealing rings 662, 664. The specimen carrier 600 includes the stick member 102 of the specimen carrier 100, described above, and a cap 604 that is substantially similar in exterior geometry to the cap 104 of the specimen carrier 100. Accordingly, the cap 604 defines a rounded end that is substantially similar in construction and function to the rounded end 130 of the cap 104. The cap 604 also forms a generally conical shaped internal channel 624 defined by an internal surface 626. The internal surface 626 includes an internal sealing surface 628 configured to interface with the external sealing surface 116 of the tip 108 of the stick member 102. Accordingly, the internal sealing surface 628 has a generally tapered, frustoconical shape. The internal sealing surface 628 defines a forward sealing ring 662 and a rearward sealing ring 664 that serve as hermetic barriers. The internal sealing surface 628 further defines a circumferential relief 666 that extends axially from an open end 668 of the cap 604 and that also defines a rearward end 676 of the internal sealing surface 628.

The internal channel 624 has a length and a minimum diameter that are about equal to the length and the minimum diameter of the internal channel 124 of the cap 104, described above. The internal sealing surface 628 has a length and a minimum diameter that are about equal to the length and the minimum diameter of the internal sealing surface 128 of the cap 104, described above. The relief 666, defining the maximum diameter of the internal sealing surface 628 at the rearward end 676, typically has a maximum diameter of about 1.9 mm to about 2.5 mm (e.g., about 2.2 mm) and a length of about 0.4 mm to about 1.0 mm (e.g., about 0.7 mm). The forward sealing ring 662 typically has a radius of curvature (i.e., with respect to a central, circular arc of the sealing ring 662) of about 0.2 mm to about 0.8 mm (e.g., about 0.5 mm), has an interior circumferential diameter (i.e., extending through a longitudinal axis of the cap 604) of about 1.7 mm to about 2.1 mm (e.g., about 1.9 mm), and is located about 3.5 mm to about 6.5 mm (e.g., at least about 5.0 mm) from the open end 668 of the cap 604. The rearward sealing ring 664 typically has a radius of curvature (i.e., with respect to a central, circular arc of the sealing ring 664) of about 0.02 mm to about 0.8 mm (e.g., about 0.5 mm), has an interior circumferential diameter (i.e., extending through the longitudinal axis of the cap 604) of about 1.8 mm to about 2.4 mm (e.g., about 2.1 mm), and is located about 1.0 mm to about 3.0 mm (e.g., at least about 2.0 mm) from the open end 668 of the cap 604. The cap 604 has a total length that is about equal to the total length of the cap 104, described above.

The cap 604 may be passed over and pressed onto the tip 108 of the stick member 102 (e.g., loaded with a specimen) at room temperature to provide interfaces 670, 672 that form respective interference fits between each of the sealing rings 662, 664 and the external sealing surface 116 of the tip 108. When the cap 604 is pressed onto the tip 108, the interference fits at the sealing rings 662, 664 cause the cap 604 to expand slightly in the regions of the sealing rings 662, 664 (e.g., the cap 104 is pushed radially outward by the tip 108 at the interfaces 670, 672). Accordingly, the cap 604 experiences localized frictional forces in the regions of the sealing rings 662, 664 without stretching of the entire cap 604. Providing the sealing rings 662, 664 (and therefore, the localized forces generated by the sealing rings 662, 664) at a sufficient distance (e.g., at least about 2.0 mm to at least about 5.0 mm) away from the open end 668 of the cap 604 can reduce or prevent stress-induced fractures that may otherwise result if such rings were located closer to the open end of such a cap. The interference fits between the sealing rings 662, 664 and the tip 108 provide both hermetic seals that prevent contamination of the internal channel 624 and frictional interfaces (e.g., securement features) that retain the cap 604 on the stick member 102.

The hermeticity of the seals can be sufficient to prevent particulates and organisms of sizes as small as about 45 nm from penetrating the seals and from therefore entering the internal channel 624 of the cap 604 and contaminating a specimen contained therein. Serial placement of the sealing ring 662 forward of the sealing ring 664 provides an additional degree of sealing that can prevent passage of particulates and organisms that manage to penetrate the sealing ring 664. The hermetic seals formed along the interfaces 670, 672 remain intact as long as the cap 604 remains pressed onto the tip 108 of the stick member 102. Furthermore, the relief 666 serves to reduce or prevent generation of excessive frictional forces that may otherwise result between the cap 604 (e.g., near the open end 668 of the cap 604) and the tip 108, thereby reducing the generation or propagation of any resulting stress fractures in the cap 604 near the open end 668.

In some embodiments, the two sealing rings 662, 662 may be made of the same material, which is different from a material of which a wall 674 of the cap 604 is made. In some embodiments, the two sealing rings 662, 664 may be made of two different, respective materials, where one or neither of the materials is the same as the material from which the wall 674 of the cap 604 is made. In some embodiments, as the elasticity of the material from which the sealing rings 662, 664 is made increases, the elastic deformation that occurs upon pressing the cap 604 onto the tip 108 increases, providing more friction at the interfaces 670, 672, a tighter seal, and improved retention of the cap 604 on the stick member 102.

In some embodiments, the cap 604 and the tip 108 of the stick member 102 may be made of the same material, thereby providing a fixed system for which, upon submersion in the low temperature substance, the interfaces 670, 672 remain fixed such that the sealing rings 662, 664 do not move substantially with respect to the external sealing surface 116 of the tip 108. In such embodiments, sealing of the specimen carrier 600 is provided by the interference fits formed at the interfaces 670, 672.

In some embodiments, any of the wall 674 and the sealing rings 662, 664 of the cap 604 may be made of one or more materials that are different from the material from which the tip 108 of the stick member 102 is made, thereby providing a dynamic system. For such embodiments in which the coefficient of thermal expansion (CTE) of one or more materials from which the wall 674 or the sealing rings 662, 664 are made is greater than the CTE of the material from which the tip 108 is made, the sealing rings 662, 664 move with respect to (e.g., shrink against) the external sealing surface 116 of the tip 108 such that the interfaces 670, 672 become dynamic upon submersion in the low temperature substance. In this manner, the sealing provided by the interference fits formed at the interfaces 670, 672 may be tightened even further due to thermal affects (e.g., as described above with respect to the specimen carrier 100) resulting from a difference in the CTE of one or more of the wall 674 and the sealing rings 662, 664 of the cap 604 and CTE of the tip 108. In some embodiments, the CTE of the one or more materials from which the wall 674 and the sealing rings 662, 664 of the cap 604 are made falls in a range of about $[100 \times 10^{-6}]/°$ C. to about $[200 \times 10^{-6}]/°$ C. (e.g., about $[150 \times 10^{-6}]/°$ C.), and the CTE of the material from which the tip 108 is made is about $[50 \times 10^{-6}]/°$ C. to about $[80 \times 10^{-6}]/°$ C. (e.g., about $[70 \times 10^{-6}]/°$ C.).

Figure 11:
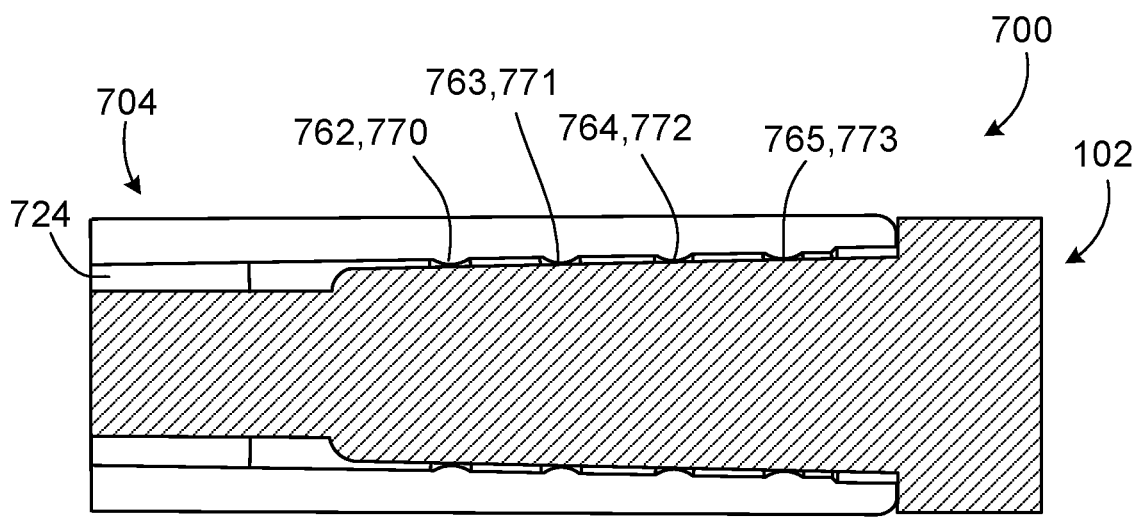
FIG. 11 is a cross-sectional view of a specimen carrier including four sealing rings, with the specimen carrier in a capped state at a relatively high temperature.

While the specimen carrier 600 has been described as including the cap 604 with two sealing rings 662, 664, in some embodiments, a specimen carrier includes a cap that has a different number of sealing rings (e.g., one, three, or four sealing rings). For example, as shown in FIG. 11, a specimen carrier 700 includes the stick member 102 of the specimen carrier 100 and a cap 704 that is substantially similar in construction and function to the cap 604 of the specimen carrier 600, except that the cap 704 includes four sealing rings 762, 763, 764, 765 that form interference fits with the external sealing surface 116 of the tip 108 along interfaces 770, 771, 772, 773 when the cap 704 is pressed onto the stick member 102. Serial placement of the sealing rings 762, 763, 764, 765 provides multiple degrees of sealing that can prevent passage of particulates and organisms that manage to penetrate any rearward sealing rings 763, 764, 765. The sealing rings 762, 763, 764, 765 may be spaced equally or unequally apart from one another. With the exception of the additional number of seals provided by the four sealing rings 762, 763, 764, 765, the specimen carrier 700 is substantially similar in construction and function to the specimen carrier 600. Accordingly, the interference fits between the sealing rings 762, 763, 764, 765 and the tip 108 provide both hermetic seals that prevent contamination of an internal channel 724 of the cap 704 and frictional interfaces that retain the cap 704 on the stick member 102.

Figure 12:
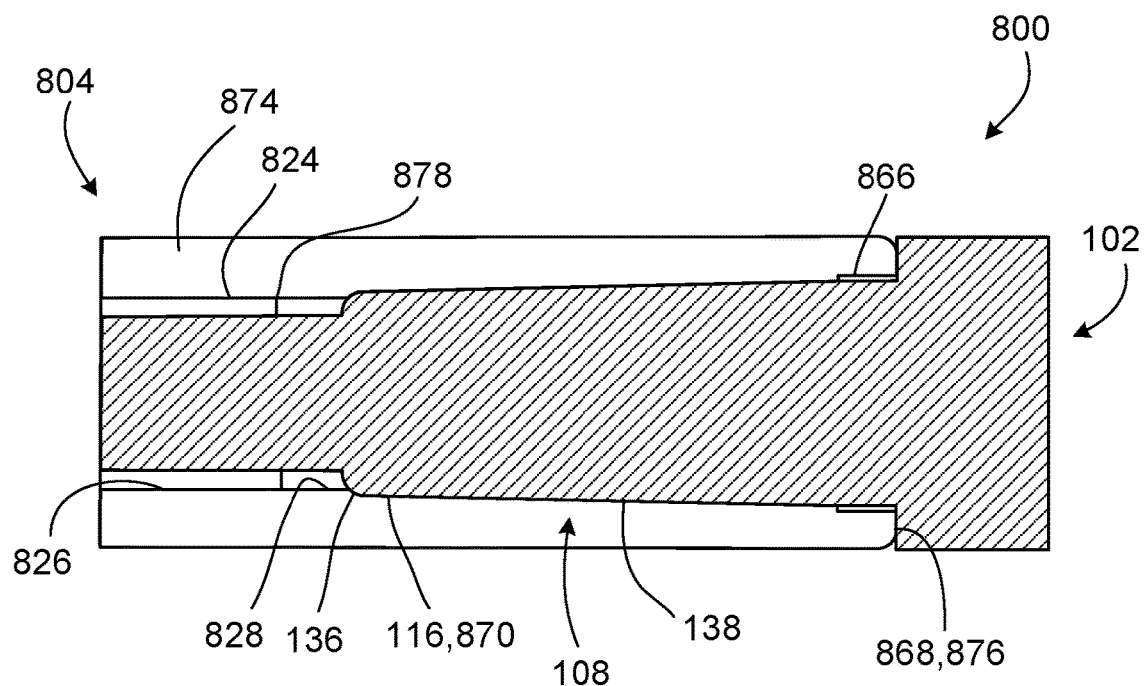
FIG. 12 is a cross-sectional view of a specimen carrier including a taper-to-taper interference fit, with the specimen carrier in a capped state at a relatively high temperature.

While the specimen carriers 600, 700 have been described as including caps with circumferential rings 662, 664, 762, 763, 764, 765 that effect sealing, in some embodiments, a specimen carrier includes a cap with a different feature that effects sealing, such as a tapered wall. For example, as shown in FIG. 12, a specimen carrier 800 includes the stick member 102 of the specimen carrier 100 and a cap 804 that provides a tapered wall 874 formed to interfere with the external sealing surface 116 of the tip 108 of the stick member 102. The cap 804 is substantially similar in exterior geometry to the cap 104, described above, and accordingly defines a rounded end that is substantially similar in construction and function to the rounded end 130 of the cap 104. The cap 804 forms a generally conical shaped internal channel 824 defined by an internal surface 826. The internal surface 826 includes an internal sealing surface 828 that extends along the tapered wall 874 of the cap 804. Accordingly, the internal sealing surface 828 and the tapered wall 874 have a generally frustoconical shape. The tapered wall 874 is dimensioned to interfere with a portion of the external sealing surface 116 of the stick member 102 when the cap 804 is pressed onto the tip 108 of the stick member 102. The internal sealing surface 828 further defines a circumferential relief 866 that extends axially from an open end 868 of the cap 804 and that therefore defines a rearward end 876 of the internal sealing surface 828.

The internal channel 824 has a length and a minimum diameter that are about equal to the length and the minimum diameter of the internal channel 124 of the cap 104, described above. The internal sealing surface 828 has a length that is about equal to the length of the internal sealing surface 128 of the cap 104. At a forward end 878, the internal sealing surface 828 typically has a minimum diameter of about 1.8 mm to about 2.2 mm (e.g., about 2.0 mm). The relief 866, defining the maximum diameter of the internal sealing surface 828 at the rearward end 876, typically has a maximum diameter of about 1.9 mm to about 2.5 mm (e.g., about 2.2 mm). The relief 866 has a length that is about equal to the length of the relief 666 of the cap 604. The cap 804 has a total length that is about equal to the total length of the cap 104.

The cap 804 may be passed over and pressed onto the tip 108 of the stick member 102 (e.g., loaded with a specimen) at room temperature to provide an interface 870 that forms an interference fit between the internal sealing surface 828 and the external sealing surface 116. When the cap 804 is passed fully over the tip 108, the interference fit extends from a forward end 136 of the external sealing surface 116 to about a midway point 138 of the external sealing surface 116. At the midway point 138, the interference between the internal sealing surface 828 and the external sealing surface 116 diminishes to about zero. The interference fit causes the cap 804 to expand slightly in the region of the interference fit along the interface 870, such that the cap 804 experiences localized frictional forces in the region without stretching of the entire cap 804. Providing the interference fit at a sufficient distance (e.g., at least about 2 mm to at least about 4 mm) away from the open end 868 of the cap 804 can reduce or prevent stress-induced fractures that may otherwise result if such an interference was located closer to the open end of such a cap. The interference fit between the tapered wall 874 and the tip 108 provides both a hermetic seal that prevents contamination of the internal channel 824 and a securement feature that retains the cap 804 on the stick member 102.

The hermeticity of the seal can be sufficient to prevent particulates and organisms of sizes as small as about 45 nm from penetrating the seal and from therefore entering the internal channel 824 of the cap 804 and contaminating a specimen contained therein. The hermetic seal formed along the interface 870 remains intact as long as the cap 804 remains pressed onto the tip 108 of the stick member 102. Furthermore, the relief 866 functions substantially similarly to the relief 666 of the cap 604, thereby reducing the generation or propagation of any resulting stress fractures in the cap 804 near the open end 868.

In some embodiments, the cap 804 and the tip 108 of the stick member 102 may be made of the same material, thereby providing a fixed system for which, upon submersion in the low temperature substance, the interface 870 remains fixed such that the tapered wall 874 does not move substantially with respect to the external sealing surface 116 of the tip 108. In such embodiments, sealing of the specimen carrier 800 is provided by the interference fit formed at the interface 870.

In some embodiments, the cap 804 may be made of one or more materials that are different from the material from which the tip 108 of the stick member 102 is made, thereby providing a dynamic system. For embodiments in which the CTE (or an aggregate CTE) of the one or more materials from which the cap 804 is made is greater than the CTE of the material from which the tip 108 is made, the tapered wall 874 moves with respect to (e.g., shrinks against) the external sealing surface 116 of the tip 108 such that the interface 870 becomes dynamic upon submersion in the low temperature substance. In this manner, the sealing provided by the interference fit formed at the interface 870 may be tightened due to thermal affects (e.g., as described above with respect to the specimen carrier 100) resulting from a difference in the CTE of the cap 804 and CTE of the tip 108. In some embodiments, the CTE of the one or more materials from which the cap 804 is made is about $[100 \times 10^{-6}]°$ C. to about $[200 \times 10^{-6}]/°$ C. (e.g., about $[150 \times 10^{-6}]/°$ C.), and the CTE of the material from which the tip 108 is made is about $[50 \times 10^{-6}]/°$ C. to about $[80 \times 10^{-6}]/°$ C. (e.g., about $[70 \times 10^{-6}]/°$ C.).

Figure 13:
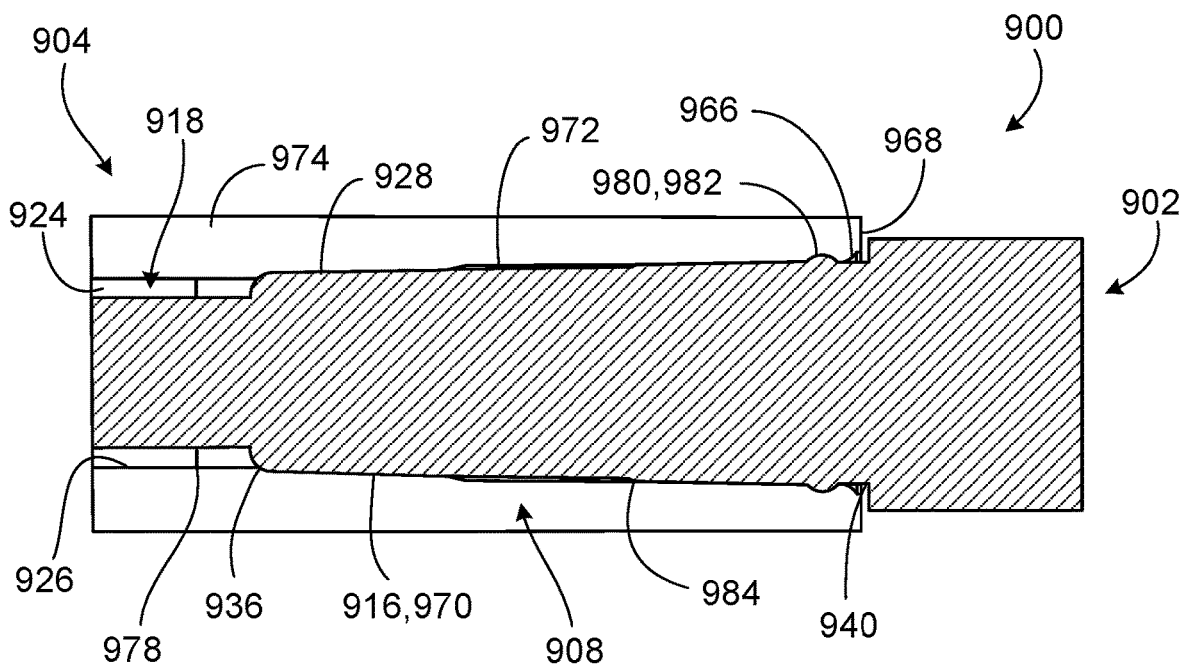
FIG. 13 is a cross-sectional view of a specimen carrier including a taper-to-taper interference fit and a separate retention ring, with the specimen carrier in a capped state at a relatively high temperature.

While the specimen carriers 600, 700, 800 have been described as including features that effect both sealing and securement of the caps 604, 704, 804 onto the stick member 102, in some embodiments, a specimen carrier includes sealing features and securement features that are isolated from one another. For example, as shown in FIG. 13, a specimen carrier 900 includes a tapered sealing structure and a retention ring that are spaced apart from each other. The specimen carrier 900 includes a stick member 902 and a cap 904.

The stick member 902 is similar in construction and function to the stick member 102 of the specimen carrier 100, described above, except that an external sealing surface 916 of a tip 908 of the stick member 902 defines a small circumferential step 984 and a circumferential snap ring 980 that are formed to engage the cap 904. The tip 908 includes a tip extension 918 that is substantially similar in construction and function to the tip extension 118 of the stick member 102, described above. The external sealing surface 916 is formed to interface with the cap 904 and has a generally frustoconical shape that has a small increase in diameter at the circumferential step 984 of the tip 908. The snap ring 980 is located near a rearward end 940 of the external sealing surface 916.

The external sealing surface 916 of the tip 908 typically has a length, a maximum diameter (excluding the diameter of the snap ring 980), and a minimum diameter that are about equal to the length, the maximum diameter, and the minimum diameter of the external sealing surface 116 of the tip 108, described above. The circumferential step 984 typically has a diameter of about 1.8 mm to about 2.4 mm (e.g., about 2.1 mm) and is located about 2.0 mm to about 3.0 mm (e.g., about 2.5 mm) from the rearward end 940 of the external sealing surface 916. The snap ring 980 typically has a radius of curvature (i.e., with respect to a central, circular arc of the snap ring 980) of about 0.1 mm to about 0.4 mm (e.g., about 0.2 mm), has a maximum circumferential diameter (i.e., with respect to a longitudinal axis of the external sealing surface 916) of about 2.1 mm to about 2.7 mm (e.g., about 2.4 mm), and is located about 0.2 mm to about 0.8 mm (e.g., about 0.5 mm) from the rearward end 940 of the external sealing surface 916. The tip 908 has a total length that is about equal to the total length of the tip 108, described above.

The tip 908 may be manufactured via a casting process or via an injection molding process (e.g., via a single injection molding process in which both a shaft of the stick member 902 and the tip 908 are manufactured as an integral component or via a separate injection molding process, following which the tip 908 is subsequently joined to the shaft as a subcomponent of the stick member 902). The tip 908 is made of one or more materials that can withstand the low temperature substance, including but not limited to polymers such as polystyrene, polypropylene, polyvinyl acetate, and polycarbonate. In some embodiments, the one or more materials are translucent or transparent. The tip 908 and the shaft may be made of the same material or made of different materials, depending on the process used to manufacture the tip 908 and the shaft of the stick member 902.

The cap 904 of the specimen carrier 900 is substantially similar in exterior geometry to the cap 104 of the specimen carrier 100, described above, and accordingly defines a rounded end that is substantially similar in construction and function to the rounded end 130 of the cap 104. The cap 904 provides a tapered wall 974 that is formed to interfere with a portion of the external sealing surface 916. The cap 904 forms a generally conical shaped internal channel 924 defined by an internal surface 926. The internal surface 926 includes an internal sealing surface 928 that extends along the tapered wall 974. Accordingly, the internal sealing surface 928 and the tapered wall 974 have a generally frustoconical shape. The internal sealing surface 928 defines a small circumferential relief 972, and the tapered wall 974 is dimensioned to interfere with a portion of the external sealing surface 916 that extends between a forward end 936 of the external sealing surface 916 and the relief 972 along the internal sealing surface 928 when the cap 904 is passed fully over the tip 908. The internal sealing surface 928 further defines a circumferential recess 982 that is positioned near an open end 968 of the cap 904 and is sized to accept the snap ring 980 of the tip 908 when the cap 904 is passed fully over the tip 908. The internal sealing surface 928 also defines a circumferential relief 966 that extends from the open end 968 of the cap 904 to the recess 982.

The internal channel 924 has a length and a minimum diameter that are about equal to the length and the minimum diameter of the internal channel 124 of the cap 104, described above. The internal sealing surface 928 has a length that is about equal to the length of the internal sealing surface 128 of the cap 104. At a forward end 978, the internal sealing surface 928 typically has a minimum diameter of about 2.0 mm to about 2.6 mm (e.g., about 2.3 mm). The relief 966, defining the maximum diameter of the internal sealing surface 928, typically has a maximum diameter of about 2.0 mm to about 2.4 mm (e.g., about 2.2 mm). The relief 972 typically has a maximum diameter that is about equal to the maximum diameter of the circumferential step 984, has a length of about 1.5 mm to about 2.1 mm (e.g., about 1.8 mm), and is located of about 1.9 mm to about 2.9 mm (e.g., about 2.4 mm) from the open end 968 of the cap 904. The recess 982 has a radius of curvature that is about equal to the radius of curvature of the snap ring 980, has a maximum circumferential diameter that is about equal to the maximum circumferential diameter of the snap ring 980, and is typically located of about 0.2 mm to about 0.8 mm (e.g., about 0.5 mm) from the open end 968 of the cap 904. The relief 966 typically has a length of about 0.1 mm to about 0.5 mm (e.g., about 0.3 mm). The cap 904 has a total length that is about equal to the total length of the cap 104.

The cap 904 may be passed over and pressed onto the tip 908 of the stick member 902 (e.g., loaded with a specimen) at room temperature to provide an interface 970 that forms an interference fit between the internal sealing surface 928 and the external sealing surface 916. When the cap 904 is passed fully over the tip 908, the interference fit extends from the forward end 936 of the external sealing surface 916 to the relief 972. In this configuration, a gap is formed between the internal sealing surface 928 and the external sealing surface 916 and extends from the relief 972 to the circumferential step 984. The interference between the internal sealing surface 928 and the external sealing surface 916 is about zero from the circumferential step 984 to the snap ring 980. The interference fit causes the cap 904 to expand slightly in the region of the interference fit along the interface 970, such that the cap 904 experiences localized frictional forces in the region without stretching of the entire cap 904. Providing the interference fit at a sufficient distance (e.g., at least about 4 mm to at least about 5 mm) away from the open end 968 of the cap 904 avoids stress-induced fractures that may otherwise result if such an interference was located closer to the open end of such a cap. The interference fit between the tapered wall 974 and the tip 908 provides a hermetic seal that prevents contamination of the internal channel 924 and provides a frictional interface (e.g., a securement feature) that retains the cap 904 on the stick member 902, while the recess 982 and the snap ring 980 together provide additional securement of the cap 904 to the stick member 902.

Furthermore, isolating the rearward snap ring 980 from the tapered wall 974 allows for hermetic sealing along the interface 970 without compromise of the seal integrity. Owing to manufacturing effects (e.g., parting lines in a mold) generated when forming the snap ring 980 on the tip 908, the integrity of the seal formed along the interface 970 could be compromised if the snap ring 980 was located closer to the tapered wall 974. Sufficiently separating the snap ring 980 from the tapered wall 974 allows the additional retention provided by the snap ring 980 without compromise of the hermetic seal formed along the interface 970. Additionally, when the cap 904 is passed over the tip 908, seating of the snap ring 980 within the recess 982 can provide a tactile feedback and/or an audible feedback to a user indicating that the cap 904 is properly secured to the stick member 902.

The hermeticity of the seal can be sufficient to prevent particulates and organisms of sizes as small as about 45 nm from penetrating the seals and from therefore entering the internal channel 924 of the cap 904 and contaminating a specimen contained therein. The hermetic seal formed along the interface 970 remains intact as long as the cap 904 remains pressed onto the tip 908 of the stick member 902. Furthermore, the relief 966 serves to reduce or prevent generation of excessive frictional forces that may otherwise result between the cap 904 (e.g., near the open end 968 of the cap 904) and the tip 908, thereby reducing the generation or propagation of any resulting stress fractures in the cap 904 near the open end 968.

In some embodiments, the cap 904 and the tip 908 of the stick member 902 may be made of the same material, thereby providing a fixed system for which, upon submersion in the low temperature substance, the interface 970 remains fixed such that the tapered wall 974 does not move substantially with respect to the external sealing surface 916 of the tip 908. In such embodiments, sealing of the specimen carrier 900 is provided by the interference fit formed at the interface 970. In some embodiments, the cap 904 may be made of one or more materials that are different from the material from which the tip 908 is made, thereby providing a dynamic system. For such embodiments in which the CTE (or an aggregate CTE) of the one or more materials from which the cap 904 is made is greater than the CTE of the material from which the tip 908 is made, the tapered wall 974 moves with respect to (e.g., shrinks against) the external sealing surface 916 such that the interface 970 becomes dynamic upon submersion in the low temperature substance. In this manner, the sealing provided by the interference fit formed at the interface 970 may be tightened due to thermal affects (e.g., as described above with respect to the specimen carrier 100) resulting from a difference in the CTE of the cap 904 and CTE of the tip 908. In some embodiments, the CTE of the one or more materials from which the cap 904 is made is about $[100 \times 10^{-6}]/°$ C. to about $[200 \times 10^{-6}]/°$ C. (e.g., about $[150 \times 10^{-6}]/°$ C.), and the CTE of the material from which the tip 908 is made is about $[50 \times 10^{-6}]/°$ C. to about $[80 \times 10^{-6}]/°$ C. (e.g., about $[70 \times 10^{-6}]/°$ C.).

Figure 14:
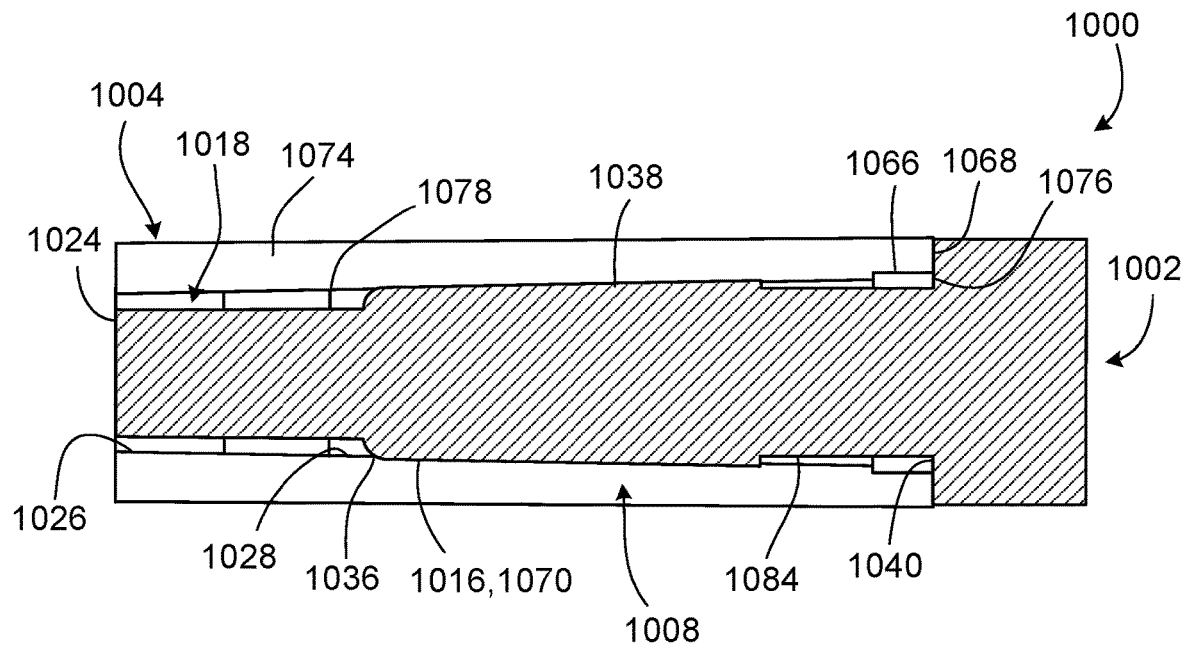
FIG. 14 is a cross-sectional view of a specimen carrier including a taper-to-taper interference fit and a separate retention relief area, with the specimen carrier in a capped state at a relatively high temperature.

While the specimen carriers 600, 700, 800, 900 have been described as including relief areas 666, 766, 866, 966, 972 on the caps 604, 704, 804, 904, in some embodiments, a specimen carrier may include a relief area on a tip of the stick member. For example, as shown in FIG. 14, a specimen carrier 1000 includes a tip with a relief area that provides a retention capability. The specimen carrier 1000 includes a stick member 1002 and a cap 1004.

The stick member 1002 is similar in construction and function to the stick member 102 of the specimen carrier 100, described above, except that an external sealing surface 1016 of a tip 1008 of the stick member 1002 defines a circumferential relief 1084 positioned rearward of a tapered portion 1038 of the external sealing surface 1016. The tip 1008 includes a tip extension 1018 that is substantially similar in construction and function to the tip extension 118 of the stick member 102, described above. The external sealing surface 1016 is formed to interface with the cap 1004 and has a generally frustoconical shape that has a small decrease in diameter along the relief 1084. The external sealing surface 1016 of the tip 1008 has a length and a minimum diameter that are about equal to the length and the minimum diameter of the external sealing surface 116 of the tip 108. The external sealing surface 1016 typically has a maximum diameter of about 1.5 mm to about 5.0 mm (e.g., about 2.0 mm) and extends about 4.0 mm to about 10.0 mm (e.g., about 6.5 mm) from a rearward end 1040 of the external sealing surface 1016. The tip 1008 has a total length that is about equal to the total length of the tip 108, described above.

The tip 1008 may be manufactured via a casting process or via an injection molding process (e.g., via a single injection molding process in which both a shaft of the stick member 1002 and the tip 1008 are manufactured as an integral component or via a separate injection molding process, following which the tip 1008 is subsequently joined to the shaft as a subcomponent of the stick member 1002). The tip 1008 is made of one or more materials that can withstand the low temperature substance, including but not limited to polymers such as polystyrene, polypropylene, polyvinyl acetate, and polycarbonate. In some embodiments, the one or more materials are translucent or transparent. The tip 1008 and the shaft may be made of the same material or made of different materials, depending on the process used to manufacture the tip 1008 and the shaft of the stick member 1002.

The cap 1004 of the specimen carrier 1000 is substantially similar in exterior geometry to the cap 104 of the specimen carrier 100, described above, and accordingly defines a rounded end that is substantially similar in construction and function to the rounded end 130 of the cap 104. The cap 1004 provides a tapered wall 1074 that is formed to interfere with a portion of the external sealing surface 1016. The cap 1004 forms a generally conical shaped internal channel 1024 defined by an internal surface 1026. The internal surface 1026 includes an internal sealing surface 1028 that extends along the tapered wall 1074. Accordingly, the internal sealing surface 1028 and the tapered wall 1074 have a generally frustoconical shape. The tapered wall 1074 is dimensioned to interfere with a portion of the external sealing surface 1016 that extends between a forward end 1036 of the external sealing surface 1016 and the relief 1084 when the cap 1004 is passed fully over the tip 1008. The internal sealing surface 1028 also defines a circumferential relief 1066 that extends from the open end 1068 of the cap 1004.

The internal channel 1024 has a length and a minimum diameter that are about equal to the length and the minimum diameter of the internal channel 124 of the cap 104, described above. The internal sealing surface 1028 has a length that is about equal to the length of the internal sealing surface 128 of the cap 104. At a forward end 1078, the internal sealing surface 1028 has a minimum diameter of about 1.8 mm to about 2.2 mm (e.g., about 2.0 mm). The relief 1066, defining the maximum diameter of the internal sealing surface 1028 at the rearward end 1076, has a maximum diameter of about 1.9 mm to about 2.5 mm (e.g., about 2.0 mm). The relief 1066 typically has a length of about 0.4 mm to about 1.0 mm (e.g., about 0.7 mm). The cap 1004 has a total length that is about equal to the total length of the cap 104.

The cap 1004 may be passed over and pressed onto the tip 1008 of the stick member 1002 (e.g., loaded with a specimen) at room temperature to provide an interface 1070 that forms an interference fit between the internal sealing surface 1028 and the external sealing surface 1016, as shown in FIG. 14. When the cap 1004 is passed fully over the tip 1008, the interference fit extends from the forward end 1036 of the external sealing surface 1016 to the relief 1084. In this configuration, a gap is formed between the internal sealing surface 1028 and the external sealing surface 1016 and extends from the relief 1084 to the open end 1068 of the cap 1004. The interference fit causes the cap 1004 to expand slightly in the region of the interference fit along the interface 1070, such that the cap 1004 experiences localized frictional forces in the region without stretching of the entire cap 1004. Providing the interference fit at a sufficient distance (e.g., at least about 1.0 mm to at least about 3.0 mm) away from the open end 1068 of the cap 1004 can reduce or prevent stress-induced fractures that may otherwise result if such an interference was located closer to the open end of such a cap.

Figure 15:
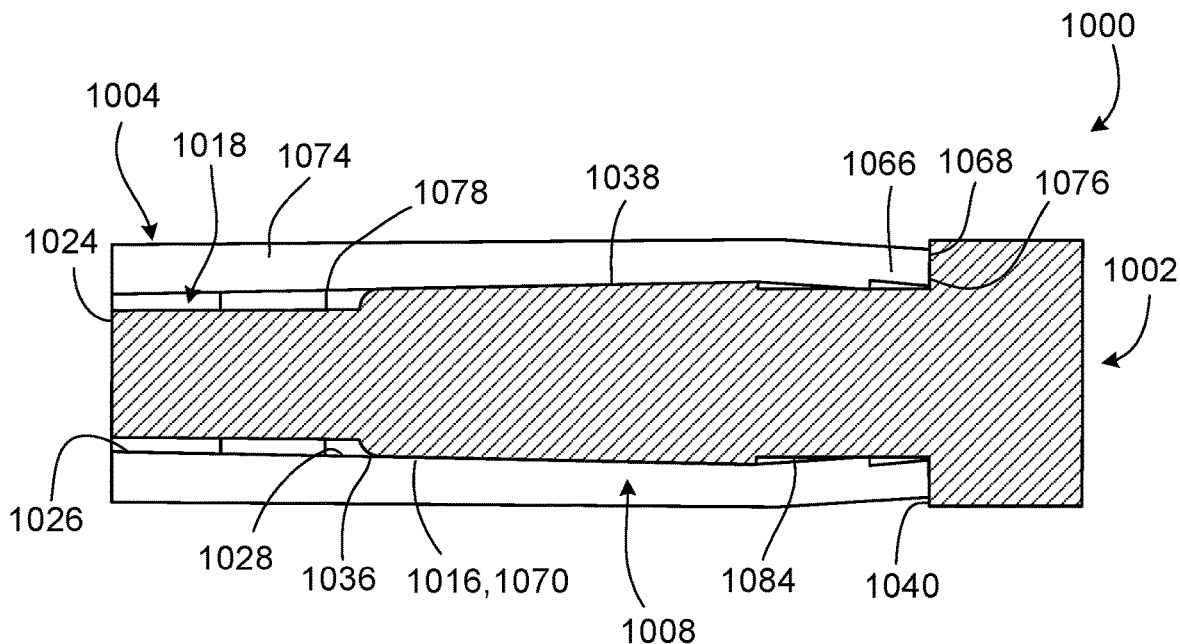
FIG. 15 is a cross-sectional view of the specimen carrier of FIG. 14 in the capped state while submerged in a low temperature substance.

The interference fit between the tapered wall 1074 and the tip 1008 provides a hermetic seal that can reduce or prevent contamination of the internal channel 1024 and a frictional interface (e.g., a securement feature) that secures the cap 1004 to the stick member 1002, while a rear portion of the tapered wall 1074 and the relief 1084 together provide additional securement that retains the cap 1004 on the stick member 1002. That is, when the specimen carrier 1000 is immersed in the low temperature substance, the rear portion of the tapered wall 1074 relaxes (e.g., collapses) into the gap formed by the relief 1084 to retain the cap 1004 on the stick member 1002, as shown in FIG. 15.

The hermeticity of the seal can be sufficient to prevent particulates and organisms of sizes as small as about 45 nm from penetrating the seals and from therefore entering the internal channel 1024 of the cap 1004 and contaminating a specimen contained therein. The hermetic seal formed along the interface 1070 remains intact as long as the cap 1004 remains pressed onto the tip 1008 of the stick member 1002. Furthermore, the relief 1066 serves to avoid generation of excessive frictional forces that may otherwise result between the cap 1004 (e.g., near the open end 1068 of the cap 1004) and the tip 1008, thereby reducing or preventing the generation or propagation of any resulting stress fractures in the cap 1004 near the open end 1068.

In some embodiments, the cap 1004 and the tip 1008 of the stick member 1002 may be made of the same material, thereby providing a fixed system for which, upon submersion in the low temperature substance, the interface 1070 remains fixed such that the a forward portion of the tapered wall 1074 does not move substantially with respect to the tapered portion 1038 of the external sealing surface 1016. In such embodiments, sealing of the specimen carrier 1000 is provided by the interference fit formed at the interface 1070. In some embodiments, the cap 1004 may be made of one or more materials that are different from the material from which the tip 1008 is made, thereby becomes dynamic upon submersion in the low temperature substance. For such embodiments in which the CTE (or an aggregate CTE) of the one or more materials from which the cap 1004 is made is greater than the CTE of the material from which the tip 1008 is made, the forward portion of the tapered wall 1074 moves with respect to (e.g., shrinks against) the tapered portion 1038 of the external sealing surface 1016 such that the interface 1070 is provided as dynamic interface. In this manner, the sealing provided by the interference fit formed at the interface 1070 may be tightened due to thermal affects (e.g., as described above with respect to the specimen carrier 100) resulting from a difference in the CTE of the cap 1004 and CTE of the tip 1008. In some embodiments, the CTE of the one or more materials from which the cap 1004 is made is about $[100 \times 10^{-6}]/° C.$ to about $[200 \times 10^{-6}]/° C.$ (e.g., about $[150 \times 10^{-6}]/° C.$), and the CTE of the material from which the tip 1008 is made is about $[50 \times 10^{-6}]/° C.$ to about $[80 \times 10^{-6}]/° C.$ (e.g., about $[70 \times 10^{-6}]/° C.$).

In some embodiments, a specimen carrier includes both a cap with sealing rings and a stick member with a relief area. For example, as shown in FIG. 16, a specimen carrier 1100 includes the cap 604 of the specimen carrier 600, described above, and the stick member 1002 of the specimen carrier 1000, described above.

Figure 16:
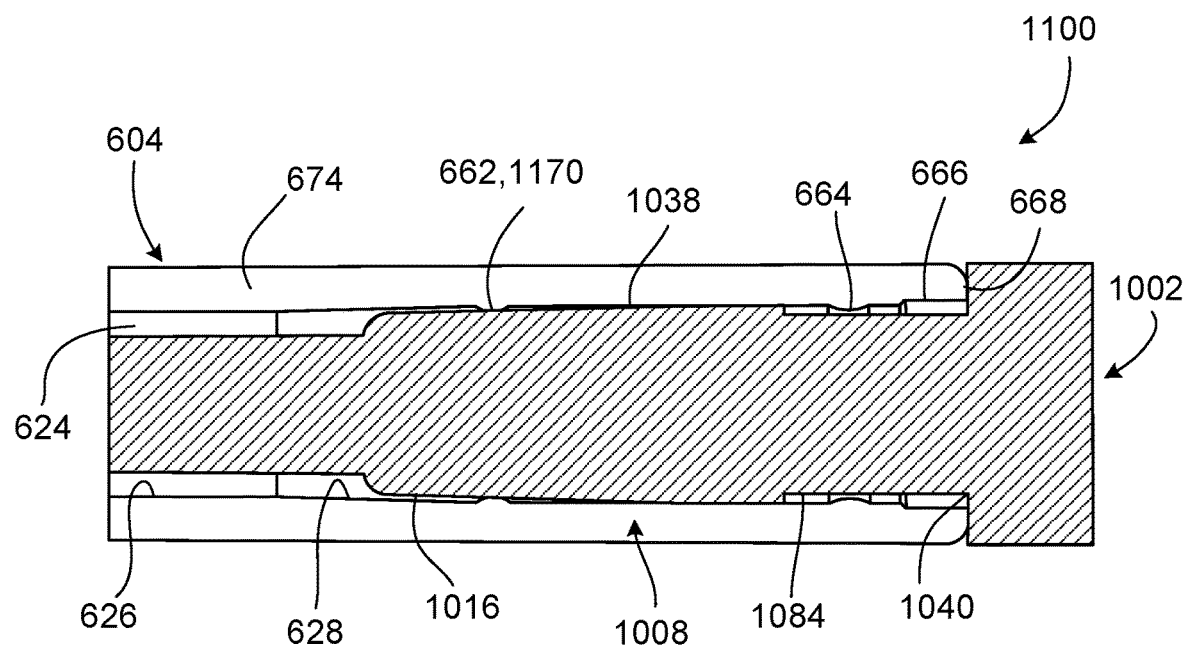
FIG. 16 is a cross-sectional view of a specimen carrier including two sealing rings and a separate retention relief area, with the specimen carrier in a capped state at a relatively high temperature.

The cap 604 may be passed over and pressed onto the tip 1008 of the stick member 1002 (e.g., loaded with a specimen) at room temperature to provide an interface 1170 that forms an interference fit between the forward sealing ring 662 and the tapered portion 1038 of the external sealing surface 1016, as shown in FIG. 16. When the cap 604 is pressed onto the tip 1008, the interference fit at the sealing ring 662 causes the cap 604 to expand slightly in the region of the sealing ring 662 (e.g., the cap 104 is pushed radially outward by the tip 1008 at the interface 1170). Accordingly, the cap 604 experiences localized frictional forces in the region of the sealing ring 662 without stretching of the entire cap 604. Providing the sealing ring 662 (and therefore, the localized forces generated by the sealing ring 662) at a sufficient distance (e.g., at least about 3.0 mm to at least about 6.0 mm) away from the open end 668 of the cap 604 can reduce or prevent stress-induced fractures that may otherwise result if such a ring was located closer to the open end of such a cap. The interference fit between the sealing ring 662 and the tip 1008 provides both a hermetic seal that prevents contamination of the internal channel 624 and a frictional interface that retains the cap 604 on the stick member 1002.

Figure 17:
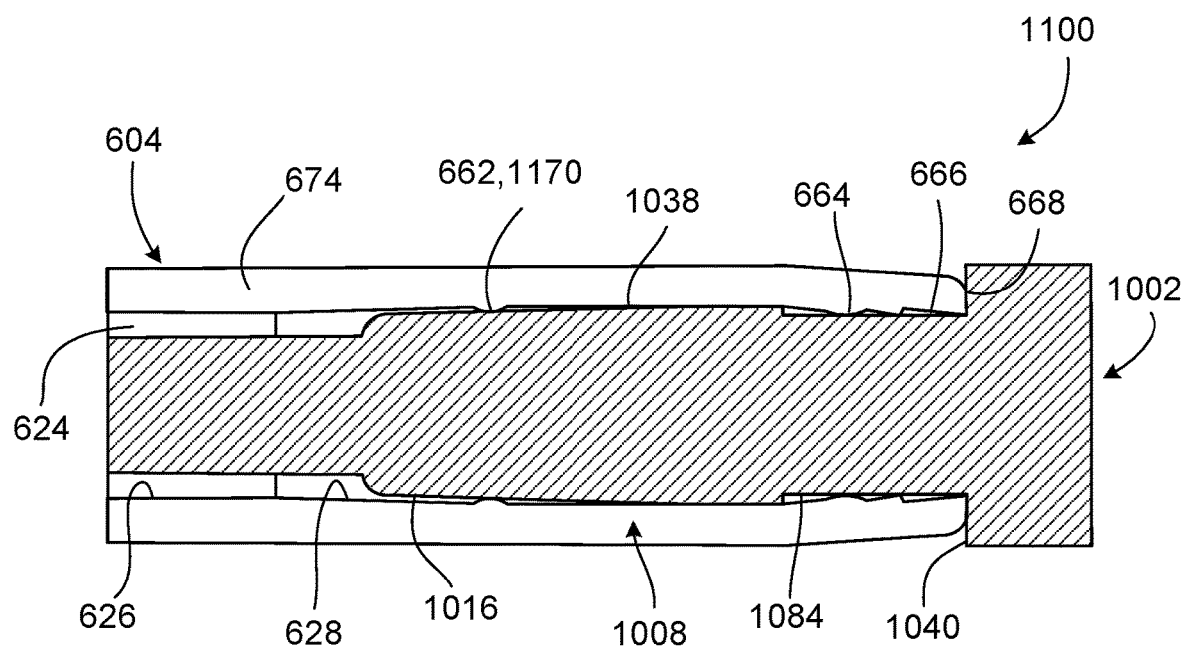
FIG. 17 is a cross-sectional view of the specimen carrier of FIG. 16 in the capped state while submerged in a low temperature substance.

Furthermore, when the cap 604 is passed over the tip 1008 of the stick member 1002, the sealing ring 664 can provide a tactile feedback and/or an audible feedback to a user as the sealing ring 664 passes along the tapered portion 1038 of the external sealing surface 1016 into the relief 1084. The feedbacks indicate to the user that the cap 604 has moved at least a certain distance with respect to the stick member 1002. A rear portion of the wall 674 and the relief 1084 together provide additional securement that retains the cap 604 on the stick member 1002. That is, when the specimen carrier 1100 is immersed in the low temperature substance, the rear portion of the wall 674 relaxes (e.g., collapses) into the gap formed by the relief 1084 to retain the cap 604 on the stick member 1002, as shown in FIG. 17.

The hermeticity of the seal can be sufficient to prevent particulates and organisms of sizes as small as about 45 nm from penetrating the seals and from therefore entering the internal channel 624 of the cap 604 and contaminating a specimen contained therein. The hermetic seal formed along the interface 1170 remains intact as long as the cap 604 remains pressed onto the tip 1008 of the stick member 1002. Furthermore, the relief 666 serves to avoid generation of excessive frictional forces that may otherwise occur between the cap 604 (e.g., near the open end 668 of the cap 604) and the tip 1008, thereby reducing or preventing the generation or propagation of any resulting stress fractures in the cap 604 near the open end 668.

In some embodiments, the cap 604 and the tip 1008 of the stick member 1002 may be made of the same material, thereby providing a fixed system for which, upon submersion in the low temperature substance, the interface 1170 remains fixed such that the a forward portion of the wall 674 does not move substantially with respect to the tapered portion 1038 of the external sealing surface 1016. In such embodiments, sealing of the specimen carrier 1100 is provided by the interference fit formed at the interface 1170.

In some embodiments, the cap 604 may be made of one or more materials that are different from the material from which the tip 1008 is made, thereby becomes dynamic upon submersion in the low temperature substance. For such embodiments in which the CTE (or an aggregate CTE) of the one or more materials from which the cap 604 is made is greater than the CTE of the material from which the tip 1008 is made, the forward portion of the wall 674 moves with respect to (e.g., shrinks against) the tapered portion 1038 of the external sealing surface 1016 such that the interface 1170 becomes dynamic upon submersion in the low temperature substance. In this manner, the sealing provided by the interference fit formed at the interface 1170 may be tightened due to thermal affects (e.g., as described above with respect to the specimen carrier 100) resulting from a difference in the CTE of the cap 604 and CTE of the tip 1008. In some embodiments, the CTE of the one or more materials from which the cap 604 is made is about $[100 \times 10^{-6}]/° C.$ to about $[200 \times 10^{-6}]/° C.$ (e.g., about $[150 \times 10^{-6}]/° C.$), and the CTE of the material from which the tip 1008 is made is about $[50 \times 10^{-6}]/° C.$ to about $[80 \times 10^{-6}]/° C.$ (e.g., about $[70 \times 10^{-6}]/° C.$).

In some embodiments, the caps 604, 704, 804, 904, 1004 of the specimen carriers 600, 700, 800, 900, 1000, 1100 may be manufactured via a casting process or via an injection molding process. The caps 604, 704, 804, 904, 1004 may be made of one or more materials that can withstand the low temperature substance, including but not limited to polymers (e.g., polystyrene, polypropylene, polyvinyl acetate, polycarbonate, and polysulfone), composite materials, ceramics, and metals (e.g. steel or titanium).

In some embodiments, the walls 674, 774, 874, 974, 1074 of the caps 604, 704, 804, 904, 1004 may include two or more layers made of different, respective materials providing an aggregate CTE that is greater than a CTE of the material from which the respective tips 108, 908, 1008 are made, as discussed above with respect to the specimen carrier 200. In such embodiments, one or more outer layers of the caps 604, 704, 804, 904, 1004 may enforce the behavior of one or more inner layers of the caps 604, 704, 804, 904, 1004 relative to the respective tips 108, 908, 1008, thereby providing a tighter closure between the external sealing surfaces 116, 916, 1016 of the tips 108, 908, 1008 and an inner-most layer of the walls 674, 774, 874, 974, 1074 of the caps 604, 704, 804, 904, 1004.

As discussed above with respect to the specimen carrier 100, the specimen carriers 600, 700, 800, 900, 1000, 1100 are sterile, single-use devices that are non-toxic to cellular and tissue specimens. The specimen carriers 600, 700, 800, 900, 1000, 1100 may be individually packaged, and both the specimen carriers 600, 700, 800, 900, 1000, 1100 and the packaging will remain sterile for a guaranteed shelf-life of the specimen carriers 600, 700, 800, 900, 1000, 1100. The specimen carriers 600, 700, 800, 900, 1000, 1100 fit within standard storage containers and other standard equipment used in ART protocols and may be used in the manner described above with respect to the specimen carrier 100 to vitrify and store reproductive cells over a period of up to about 40 years.

While the specimen carriers 600, 700, 800, 900, 1000, 1100 have been described as including the tips 108, 908, 1008 of the stick members 102, 908, 1008, in other embodiments, a specimen carrier may include any one of the caps 604, 704, 804, 904, 1004 in combination with a stick member that has any one of the tips 108, 308, 408, 508.

In some embodiments, a specimen carrier may include any one of the tips 108, 308, 408, 508, 908, 1008 and a cap that is similar in construction and function to any of the caps 104, 604, 704, 804, 904, 1004, except that the cap further includes a frangible interface that prevents multiple uses of the cap. Prior to and during securement of the cap to the stick member, the frangible interface may remain intact. However, upon removal of the secured cap, the frangible interface may tear or separate, indicating to a user that the single-use cap has been previously used.

In some embodiments, any of the specimen carriers 100-1100 may include a marking (e.g., a bar code or a series of alphanumeric characters) on a component (e.g., an external surface of the cap or the shaft of the stick member) of the specimen carrier that provides patient identification information.

What is claimed is:

1. A specimen carrier, comprising:
   an elongate member defining an external sealing surface and a support surface upon which a specimen can be carried, the elongate member defining a flat proximal recess that provides a first tactile feedback to a user of the specimen carrier, and the elongate member comprising a first material having a first coefficient of thermal expansion; and
   a cap configured to be passed over a portion of the elongate member to close a region of the cap that surrounds the specimen when the cap is passed over the portion of the elongate member, the cap defining an internal sealing surface formed complementary to the external sealing surface, the cap defining a convex distal end that provides a second tactile feedback to the user for tactilely differentiating the elongate member from the cap for appropriate handling of the specimen carrier, and the cap comprising a second material having a second coefficient of thermal expansion that is greater than the first coefficient of thermal expansion, such that when the portion of the elongate member is covered with the cap and the portion of the elongate member and the cap are together placed in a cooling substance, the internal sealing surface of the cap compresses the external sealing surface of the elongate member to form a hermetic seal along an interface formed between the internal sealing surface and the external sealing surface.

2. The specimen carrier of claim 1, wherein the cap further defines an internal channel forming the region of the cap that surrounds the specimen when the cap is passed over the portion of the elongate member, the internal sealing surface forming a part of the internal channel.

3. The specimen carrier of claim 1, wherein the cap is configured to be passed over the portion of the elongate member in an ambient environment of a first temperature, and the cooling substance is of a second temperature that is lower than the first temperature.

4. The specimen carrier of claim 3, wherein the elongate member and the cap are configured such that, at the first temperature, the interface formed between the external and internal sealing surfaces comprises an interference fit.

5. The specimen carrier of claim 1, wherein the external and internal sealing surfaces have a frustoconical shape.

6. The specimen carrier of claim 1, wherein the first and second coefficients of thermal expansion are independent of a dimensional unit of the first and second materials, respectively.

7. The specimen carrier of claim 1, wherein the first material is a transparent or translucent material.

8. The specimen carrier of claim 1, wherein the hermetic seal prevents organisms and particulates as small as about 45 nm from entering the region of the cap that surrounds the specimen when the cap is passed over the portion of the elongate member and the portion of the elongate member and the cap are together disposed in the cooling substance.

9. The specimen carrier of claim 1, wherein the elongate member comprises a shaft configured for handling of the elongate member.

10. The specimen carrier of claim 9, wherein the shaft comprises a plurality of surface facets defining a hexagonal cross-sectional shape that is configured to prevent the elongate member from rolling on a surface.

11. The specimen carrier of claim 9, wherein the shaft defines the flat proximal recess that provides the first tactile feedback to the user of the specimen carrier.

12. The specimen carrier of claim 1, wherein the cap defines a tapered exterior profile terminating at the convex distal end.

13. The specimen carrier of claim 1, wherein the elongate member defines a vertical wall that shields the support surface.

14. The specimen carrier of claim 1, wherein the specimen comprises one or more reproductive cells.

15. The specimen carrier of claim 1, wherein the cooling substance is a vitrification medium.

16. The specimen carrier of claim 1, wherein the cooling substance comprises liquid nitrogen.

17. The specimen carrier of claim 1, wherein the cap further comprises a third material surrounding the second material, the third material having a third coefficient of thermal expansion that is greater than the second coefficient of thermal expansion.

18. The specimen carrier of claim 17, wherein the second and third materials together provide an aggregate coefficient of thermal expansion that is greater than the second coefficient of thermal expansion and less than the third coefficient of thermal expansion.

19. The specimen carrier of claim 1, wherein the specimen carrier is configured to preserve the specimen in a viable state within the cooling substance over a period of at least 40 years.

20. The specimen carrier of claim 11, wherein the recess further provides a visual indication that the specimen carrier is oriented correctly while submerged in the cooling substance.

21. The specimen carrier of claim 11, wherein the recess comprises a textured profile on which information can printed.

* * * * *